(12) United States Patent
Dimitrijevich et al.

(10) Patent No.: US 6,471,958 B2
(45) Date of Patent: Oct. 29, 2002

(54) NON-CONTRACTING TISSUE EQUIVALENT

(75) Inventors: S. Dan Dimitrijevich, Bedford; Robert W. Gracy, Fort Worth, both of TX (US)

(73) Assignee: University of North Texas Health Science Center, Fort Worth, TX (US)

(*) Notice: Subject to any disclaimer, the term of this patent is extended or adjusted under 35 U.S.C. 154(b) by 0 days.

(21) Appl. No.: 09/775,843

(22) Filed: Feb. 1, 2001

(65) Prior Publication Data

US 2002/0028192 A1 Mar. 7, 2002

Related U.S. Application Data

(63) Continuation-in-part of application No. 09/046,755, filed on Mar. 24, 1998, now abandoned.

(51) Int. Cl.[7] .................................................. C12N 5/08
(52) U.S. Cl. ...................... 424/93.7; 435/325; 435/371; 435/373; 435/395; 435/397
(58) Field of Search .......................... 530/356; 435/395, 435/325, 373, 397, 371; 424/93.7

(56) References Cited

U.S. PATENT DOCUMENTS 4,485,096 A * 11/1984 Bell ............................ 424/532

OTHER PUBLICATIONS

Finesmith et al., Journal of Cellular Physiology 144: 991–07 (1990).*
Montesano et al., PNAS USA 85: 4894–4897 (Jul. 1988).*
Clark et al., Journal of Clinical Investigation 84: 1036–1040 (Sep. 1989).*

* cited by examiner

*Primary Examiner*—Jean C. Witz
(74) *Attorney, Agent, or Firm*—Olson & Hierl, Ltd.

(57) ABSTRACT

The present invention provides a non-contracting tissue equivalent comprising at least one cellular component and at least one non-cellular component. The tissue equivalent closely resembles normal tissue in being substantially non-contracting. In addition, the non-contracting tissue equivalent is translucent, allowing direct visual observation of the different layers of cells in the tissue equivalent. The non-contracting tissue equivalent is useful for a variety of complete tissue replacements including skin and cornea. The non-contracting tissue equivalent is useful for in vitro testing, evaluation and screening of potential pharmaceuticals or consumer products, production of biocompatible clinical products for tissue replacement and augmentation, and research studies on fundamental aspects of tissue structure and function. The capability for direct visual observation of layers of cells permits manual or automated assessment of important biological parameters of the tissue, including cell viability, proliferation, motility, and differentiation.

36 Claims, 24 Drawing Sheets

NON-CONTRACTING TISSUE EQUIVALENT

This application is a continuation-in-part of U.S. Ser. No. 09/046,755, filed Mar. 24, 1998 now abandoned.

FIELD OF THE INVENTION

The invention relates generally to multicellular tissue-like compositions.

BACKGROUND OF THE INVENTION

Tissue equivalents are three-dimensional living multicellular tissue-like compositions. While these tissue equivalents have many uses, including tissue transplantation, screening and evaluation of new drugs, previous tissue equivalents have had limited utility because they contracted. For example, a tissue equivalent comprising a collagen matrix can exhibit as much as about 80% linear shrinkage, i.e., can contract to as little as twenty percent of the original diameter within a period of a few hours. This contraction produces a dense, opaque matrix which prevents the visualization of the contained cells by optical microscopy. The resulting tissue equivalent may resemble normal scar tissue more than the desired normal healthy tissue. The factors responsible for such contraction have not been systematically evaluated and studied, but may include collagen concentration and cell numbers.

In general, tissue equivalents are produced by combining at least one cellular component with at least one noncellular component. The design and construction of tissue equivalents is a branch of tissue engineering, which can be defined as the application of scientific principles to the design, construction modification, growth and maintenance of living tissues to form the desired composition.

Tissue-equivalents have numerous uses including: sources of tissue for transplantation; systems for screening and evaluating potential drugs, cosmetics and other consumer products; model systems for the study of multicellular processes such as wound healing; systems for establishing optimal conditions for trans-tissue delivery of hormones, cytokines or other biologically active materials and systems for introducing cells genetically engineered to produce a desired substance. It would be desirable to use such tissue equivalents to decrease dependency on cadaver tissue for grafts and transplants and to reduce dependency on animal testing in the development of new pharmaceuticals and consumer products.

"Tissue equivalent" as used herein includes, but is not limited to, artificially produced epithelial tissue, skin, cornea, connective tissue, cartilage, bone, and the like (see for example, U.S. Pat. Nos. 4,485,096; 4,485,097; 4,546,500; 4,539,716; 4,604,346; 4,835,102).

The cellular component of tissue equivalents may be derived from a number of sources. The cells comprising the cellular component may be autologous, that is, the donor and the recipient may be the same person. The cells are processed, incorporated into the non-contracting tissue equivalent, and transplanted back into the donor as part of the tissue equivalent. Alternatively, the cells may be allogenic, that is taken from a different donor than the recipient of the transplanted tissue equivalent, where both the donor and recipient are members of the same species. The cells also may be xenogeneic, i.e., derived from a donor of a different species from the recipient. In each of these cases, treatments are known in the art that reduce the likelihood of rejection or control the differentiation of the cellular component. Human cells, i.e., either autologous or allogenic cells, are preferred.

The noncellular component of tissue equivalents may comprise one or more of a group of compounds, including compounds normally secreted by cells to form a naturally occurring extracellular matrix. Suitable compounds include the collagens.

The collagens are a family of fibrous proteins that are secreted by connective tissue cells, as well as by a variety of other cell types. See generally, Alberts, B., et al., *Molecular Biology of the Cell*, 3rd Ed., Garland Publishing, New York (1994) pp. 978–984. The characteristic feature of a typical collagen molecule is its long, stiff, triple-stranded helical structure, in which three collagen polypeptide chains, called $\alpha$ chains, are wound around one another in a rope-like superhelix. About 25 distinct collagen $\alpha$ chains have been identified, each encoded by a separate gene.

About fifteen different types of collagen have been described, which are characteristically composed of different combinations of specific $\alpha$ chains. Type I collagen (collagen I) is the principal collagen of skin, tendon, ligaments, cornea, internal organs and bone. Collagen I is by far the most common, accounting for about 90% of body collagen. The $\alpha$ chain composition of collagen I is $[\alpha 1(I)]_2 \alpha 2(I)$.

Other fibrillar collagens are types II, III, V, VII and XI. Type II collagen (collagen II) cartilage, composed of $[\alpha 1(II)]_3$ $\alpha$ chains, is found in cartilage, the intervertebral discs of the spine and the vitreous humor of the eye. Type III collagen (collagen III), $[\alpha 1(III)]_3$, is found in skin, blood vessels and internal organs. Type V collagen (collagen V), $[\alpha 1(V)]_2 \alpha_2(V)$, is found in the same tissues as type I collagen. Type XI collagen (collagen XI), $\alpha 1(XI)\alpha 2(XI)\alpha 3(XI)$, is found in the same tissues as collagen I. Alberts, et al., page 980.

In contrast to the above fibrillar collagens, network-forming collagens form a felt-like sheet or meshwork instead of rope-like fibers. An important network-forming collagen is collagen IV, $[\alpha 1(IV)]_2 \alpha 2(IV)$, which forms the basal lamina. The basal lamina, sometimes called the basement membrane, is a thin mat of extracellular matrix that separates the epithelium from the underlying stroma/connective tissue. The basal lamina also separates many other types of cells, such as muscle cells and fat cells, from connective tissue.

In previous tissue equivalents, for example those described in Clark et al., J. Clin. Invest. 84: 1036–1040 (1989) and Montesano et al., Proc. Nat. Acad. Sci. U.S.A. 85: 4894–4897 (1988), the collagen matrix contracts after formation to a fraction of its original size (typically to about twenty percent of the original diameter) over a period of up to 48 hours. The contraction of the tissue equivalent as a whole follows the contraction of the collagen matrix. As a result, the matrix condenses forming a dense, opaque tissue which prevents visualization of the contained cells by transmitted light or fluorescence microscopy. The multiple factors responsible for contractions have not been studied systematically but it has been proposed that they include cell number and collagen concentration. In addition, unknown combinations of cytokines, such as presumably present in exogenously supplied serum such as fetal bovine serum (FBS) may be responsible for contraction.

Contraction of tissue equivalents may be desirable for some limited number of uses, for example, in wound closure or scar formation. However, extensive contraction produces an abnormally dense scar-like tissue that impedes normal tissue functions such as epithelialization, vascularization, pigmentation and hair growth. Contraction of tissue equivalents is thus a problem for which a solution has been sought for several years.

Previous non-contracting tissue equivalents have been constructed using pre-formed collagen sponge matrices. Collagen sponge matrices are composed of insoluble, covalently-linked, solid collagen fibrils. Covalent cross-links are formed between collagen fibrils by chemical reactions and thus cannot be readily reversed. The physical form of collagen sponges produced by chemical cross-linking can only be altered by digestion with collagenase, an enzyme which degrades collagen into its component amino acids. In addition, collagen sponges may retain the toxic chemical reagents used in cross-linking, such as aldehydes, which may leach into the host tissues, causing adverse reactions.

What is needed is a non-contracting tissue equivalent that provides dimensional stability and permits the monitoring of the functions of viability of the cellular component.

SUMMARY OF THE INVENTION

The present invention provides a method for producing a substantially non-contracting tissue equivalent comprising a three-dimensional, dimensionally substantially stable collagenous matrix populated by mesenchymal cells, which cells can be from a variety of sources. The collagenous matrix is substantially stable dimensionally and does not contract, i.e., does not substantially change in wet weight, volume and density, for at least twenty one days. The substantially non-contracting tissue equivalent of the present invention can be maintained in vitro for at least six months.

The tissue equivalent so produced comprises at least one non-cellular component and at least one cellular component. Suitable non-cellular components are naturally occurring collagenous materials such as collagen I, collagen III, collagen IV, hyaluronic acid, chitosan, chondroitin-6 sulfate, fibrin, fibronectin, and mixtures thereof. Collagenous materials suitable as matrix components preferably are chosen from the group consisting of collagen I, collagen III, collagen IV, fibrin, fibronectin and mixtures thereof. One particularly preferred matrix component is collagen I.

The non-cellular component can also include synthetic materials in addition to, or instead of, the collagenous materials. Suitable such synthetic materials include polyglycolic acid, polylactic acid, polyhydroxybutyrate, and the like.

Preferably the tissue equivalents of the present invention have a non-cellular component that is a collagenous matrix and a cellular component that comprises mesenchymal cells such as fibroblasts, and the like. Typically a mixture of collagen and fibroblasts is allowed to thicken, preferably by the gelation (fibrillogenesis) of the collagen.

Suitable cellular components are mesenchymal cells selected from cells of multicellular animals, preferably from mammalian cells, and are optimally human cells. The human cells may be autologous, that is, derived from the same individual who will ultimately receive a graft of the tissue equivalent. Alternatively, cells may be selected that originate from another human or from individuals of another species. If non-autologous cells are used, appropriate means of suppressing any immune response to the tissue equivalent are known to one of ordinary skill.

Suitable are mesenchymal cells which may originate from a variety of tissues and are chosen preferably from the group consisting of fibroblasts, keratinocytes, melanocytes and mixtures thereof. One such preferred cellular component is human fibroblasts.

A three-dimensional tissue equivalent can be formed by a method comprising the steps of combining an aqueous suspension of at least one mesenchymal cell type with at least one soluble collagenous material and gelling the soluble collagenous material to form a substantially non-contracting tissue equivalent constituted by a collagenous matrix with mesenchymal cells. Preferably the soluble collagenous component is collagen I, which gels at about pH 7 upon warming to about body temperature to form a substantially non-contracting translucent matrix. This translucent matrix is hydrophilic, free from covalent crosslinks, and can be liquified in an acidic pH environment.

The basic three-dimensional tissue equivalent can serve as the foundation for the construction of more complex products comprising additional cellular components and as well as collagenous components. The basic three-dimensional tissue equivalent is produced by a method wherein an aqueous suspension of mesenchymal cells in a nutrient medium is combined with at least one soluble collagenous component at a temperature below about ambient temperature and the resulting admixture is solidified by gelation at about 37° C. and at a pH of about 7 to a translucent matrix that contains mesenchymal cells. A further collagenous material and additional mesenchymal cells can be added to form a substantially non-contracting multicellular tissue equivalent, if desired.

In one embodiment, the first cellular component comprises fibroblasts, a first soluble extracellular matrix component comprises collagen I, a second cellular component comprises keratinocytes, and a second soluble extracellular matrix component comprises collagen IV. In another embodiment, a first cellular component comprises corneal fibroblasts, e.g., keratocytes, and a first soluble extracellular matrix component comprises collagen I, a second cellular component comprises corneal epithelial cells, and a second soluble extracellular matrix component comprises collagen IV. In a further embodiment, a first cellular component comprises corneal fibroblasts such as keratocytes and a first soluble extracellular matrix component comprises collagen I, a second cellular component comprises corneal endothelial cells, and a second soluble extracellular matrix component comprises mixture of collagen I, fibronectin, and laminin.

Additional compatible cellular components and non-cellular components may also be used in forming the tissue equivalent. For example, a tricellular three-dimensional tissue equivalent is produced by contacting an aqueous suspension of a first cellular component with at least one soluble collagenous matrix component; dispersing the first cellular component in the soluble matrix component; and gelling the resulting admixture to form a dermal equivalent having a first or top surface and a second or bottom surface. The top surface of the dermal equivalent is then contacted with a solution of another cellular component, and optionally with extracellular matrix components, to form a layer thereof which upon gelling forms a substantially non-contracting bicellular three-dimensional tissue equivalent. The non-contracting bicellular three-dimensional tissue equivalent is then similarly contacted with another set of cellular and extracellular components to form a tricellular, three-dimensional tissue equivalent. In one illustrative embodiment, the initial cellular component comprises fibroblasts, and the extracellular collagenous matrix component therefor comprises collagen, another cellular component comprises melanocytes, another soluble extracellular collagenous matrix component comprises collagen IV, and a further cellular component comprises keratinocytes.

The substantially non-contractile characteristic of this tissue equivalent is independent of cell density in the range of about $1.0 \times 10^5$ to about $5.0 \times 10^5$ cells/ml, and is independent of collagen concentration in the range of about 3 to about 5 mg/ml. The cells which are used to establish the non-contracting tissue equivalent may be from any passage but early passage cells (up to passage 5) are preferred, and may be taken from donors of any age and sex. Cells from the skin of young donors (e.g., infant) are preferred, however.

The substantially non-contractile quality of the tissue equivalent is characterized by the lack of substantial change in wet weight, volume and density over time. More specifically, the non-contractile quality of the tissue equivalent is characterized by less than about 5% shrinkage over a period of about twenty-one days. An additional important unique advantage of the non-contracting tissue equivalent is its translucency, which allows direct visual observation of its component cells by optical microscopy.

The non-contracting tissue equivalent provided by the present invention more closely resembles normal tissue than any tissue equivalent previously described. The cellular component of this tissue equivalent is quiescent until stimulated. Appropriate stimuli can induce the non-contracting tissue equivalent to undergo cell division, synthesize extracellular matrix macromolecules, migration of cells, or undergo contraction. The non-contracting tissue equivalent can support growth and differentiation of epithelial cells as well as the growth of endothelial cells. Both the epithelial and the endothelial surfaces thus produced on the non-contracting tissue equivalent display characteristic histological features of normal tissues.

The non-contracting tissue equivalent is hydrophilic and translucent, permitting the visual observation of the cellular components by transmitted light and fluorescence microscopy. Cellular viability, cell motility, as well as cellular growth and differentiation can be directly observed. Thus, quantitative evaluation of the status of cells of the non-contracting tissue equivalent can be conveniently and rapidly assessed by either manual or automated methods.

In contrast to the contracting tissue equivalents that lose water, resulting in the condensation of the matrix, equivalent to the formation of a scar, the matrix of the non-contracting tissue equivalent remains substantially hydrated, and thus maintains a greater natural permeability to exogenous materials such as nutrients or drugs. This greater natural permeability of the non-contracting tissue equivalent also provides a more realistic system in which to study the processes of tissue contraction and consequent scarring. Thus, the non-contracting tissue equivalent of the present invention provides a useful system for the study of fundamental mechanisms and therapeutic approaches in wound healing.

The non-contracting tissue equivalent of the present invention is generally useful in supporting the growth and differentiation of various epithelial and endothelial cells. The non-contracting tissue equivalent, when used as a support for epithelial cells, can support cellular differentiation without the use of exogenous agents, such as retinoic acid.

The non-contracting tissue equivalent can be used as a transplant material, providing a barrier that assists the recipient in maintaining proper hydration, excluding pathogens and assisting thermoregulation. Mechanically, the non-contracting tissue equivalent is robust enough to survive manual manipulation.

The non-contracting tissue equivalent can also be used as a system for screening of potential drugs and consumer products. This tissue equivalent can be used to test substances administered in either a systemic mode (test substance applied to the endothelial side) or a topical mode (test substance applied to the epithelial side).

The non-contracting tissue equivalent can also be used as an implantable source of exogenous substances, such as substances used to facilitate processes such as wound healing. Cell types that naturally secrete useful substances, such as cytokines, can be incorporated as part or all of the cellular component of the tissue equivalent. Alternatively, cells such as fibroblasts that have been genetically engineered to enhance normal expression of a product or to express a recombinant protein, can be incorporated as part or all of the cellular component of the tissue equivalent.

The non-contracting tissue equivalents are also useful for studies of the effects of drugs, cosmetics and other pharmaceutical agents by more invasive methods. For example, following exposure to various agents, the non-contracting tissue equivalents may be frozen, embedded in a suitable embedding composition and sectioned for histochemical determination of cellular or extracellular enzymatic activities, and peptide and protein functionality. Alternatively, the tissue equivalents may be fixed, embedded in paraffin or other suitable embedding composition and sectioned for examination using optical microscopy. Histochemical, immunohistochemical, and immunofluorescent methods to establish the presence of absence of specific proteins, glycoproteins, and proteoglycans may be used on frozen sections or sections that have been treated to remove the matrix of embedding compound. Sections of the non-contracting tissue equivalent can also be used to assess gene expression by in situ hybridization with nucleotide probes complementary to specific nucleic acid sequences.

The fixed tissue equivalents may also be embedded in plastic resins, thin-sectioned and observed using transmission electron microscopy for evaluation of ultrastructural changes. Several techniques permit one skilled in the art to visualize antibody or oligonucleotide probes. For example, treatment of the tissue with gold labeled antibodies (immunogold labeling) can visualize antibodies to specific proteins, glycoproteins, and proteoglycans and precisely delineate minute changes in their localization or quantities. Similar precision in monitoring nuclear events can be attained by using labeled oligoriboprobes. Gold, alone or with silver enhancement, may be localized in the cells and tissues because it is opaque to the beam bombarding the specimen. Surfaces of the fixed tissues may be coated with osmium and examined by scanning electron microscopy because it is opaque to the beam bombarding the specimen. Such techniques allow evaluation of changes in the ultrastructural features of the surface of the tissue equivalent caused by the exposure to a variety of environments or materials.

In addition to the above methods for directly assessing the effects of external conditions on the tissue equivalents, the individual constituents of the tissue equivalent can be dissociated and the individual components thereof isolated and analyzed separately. For example, the collagenous matrix of the tissue equivalent can be dissociated by mild treatment with collagenase. This also is much more accurate and reproducible on a non-contracting tissue equivalent than on a contracted, scar-like matrix. The cell numbers can be determined by usual methods, e.g., using a hemocytometer or flow cytometry.

Cellular and extracellular changes in molecular composition can be quantitated by analytical biochemical or molecular biology methods. Cellular and molecular processes can also be labeled, radioisotopically or otherwise to increase sensitivity of methods for quantitative or qualitative analysis.

The status of the cellular and extracellular components of the non-contracting connective tissue equivalents can be readily evaluated since they are translucent. These unique features allow direct visual observation of the cellular component of the tissue equivalents by light microscopy. If the cells are labeled with a vital dye such as neutral red, an inclusion viability dye, and exposed to different agents, optical microscopic evaluation allows a qualitative picture of the consequences. In this example, neutral red staining demonstrates cellular viability and failure to take up neutral red would indicate toxicity. Due to the translucency of the non-contracting tissue equivalent, it is possible to scan an optical field and determine the number of total cells and the number of viable cells. This procedure can be conducted either manually or by automated scanners. By scanning the matrix in three dimensions, changes in the cell number or cellular orientation can be determined. The present invention thus provides a rapid method for assessing agents which may be toxic or otherwise change the physiological status of a tissue.

Similarly, as seen in FIG. 5, confocal microscopy with computer assisted image processing can be used to quantitate changes in the numbers of viable cells, if the cells are labeled with suitable fluorescent markers. Cell Tracker™ Orange, 5-(and 6-)-(((4-chloromethyl)benzyol)amino)-tetramethylrhodamine (Molecular Probes, Eugene, Oreg.), is a preferred fluorescent reagent to demonstrate viable cells, since only living cells possess the intracellular enzymes required to convert the reagent to the fluorescent product that is detected. Labeling cells with fluorescent markers also permits the observation of changes in the orientation or migration of the cells in addition to determining viability. When a suitable mechanical stage and a suitable microscopy system are used, automated assessment of cell viability and growth can be monitored easily due to the translucent nature of the non-contracting tissue equivalent.

The thickness of the tissue equivalent may impose a limit of this methodology, since the ability to detect labeled cells is impaired by background autofluorescence that increases with thickness. However, single/double photon confocal microscopy can overcome the problem of background autofluorescence. In single/multiple photon confocal microscopy, the tissue is scanned by a laser that only excites the fluorescent marker and background autofluorescence in the plane of the scan, thereby forming optical sections and increasing the effective brightness of the labeled cell compared to the background autofluorescence. Multiple photon evaluation utilizing cells' innate fluorescence, e.g., that due to the NAD/NADH system can be utilized as well. The latter approach could be applied to living tissue equivalents or to organisms in vivo without having to prelabel fluorescently the cells.

The translucence of the non-contracting tissue equivalent facilitates types of monitoring that support spectroscopic analyses. The non-contracting tissue equivalent also is ideal for other minimally invasive methods, such as, studies of metabolic processes using nuclear magnetic resonance (nmr) spectroscopy and metabolic substrates labeled with paramagnetic stable isotopes. Natural abundance of paramagnetic stable isotopes can also be used for monitoring processes of interest.

The non-cellular component and the incorporated cellular component may remain attached to the vessel in which it was formed or it may detach from the vessel and float in the culture medium. In the latter case, these tissue equivalents are referred to as "floating cultures" or "raft cultures."

BRIEF DESCRIPTION OF THE DRAWINGS

In the Drawings,

(FIG. 4A, 25× magnification; FIG. 4B 100× magnification);

FIG. 6 is a photograph of a bicellular human skin equivalent prepared with the non-contracting tissue equivalent, where

FIG. 25 is a histogram showing showing contraction of dermal equivalents for Run #2 (Example 20) over a 30-hour period.

DETAILED DESCRIPTION OF THE INVENTION

Figure 1:
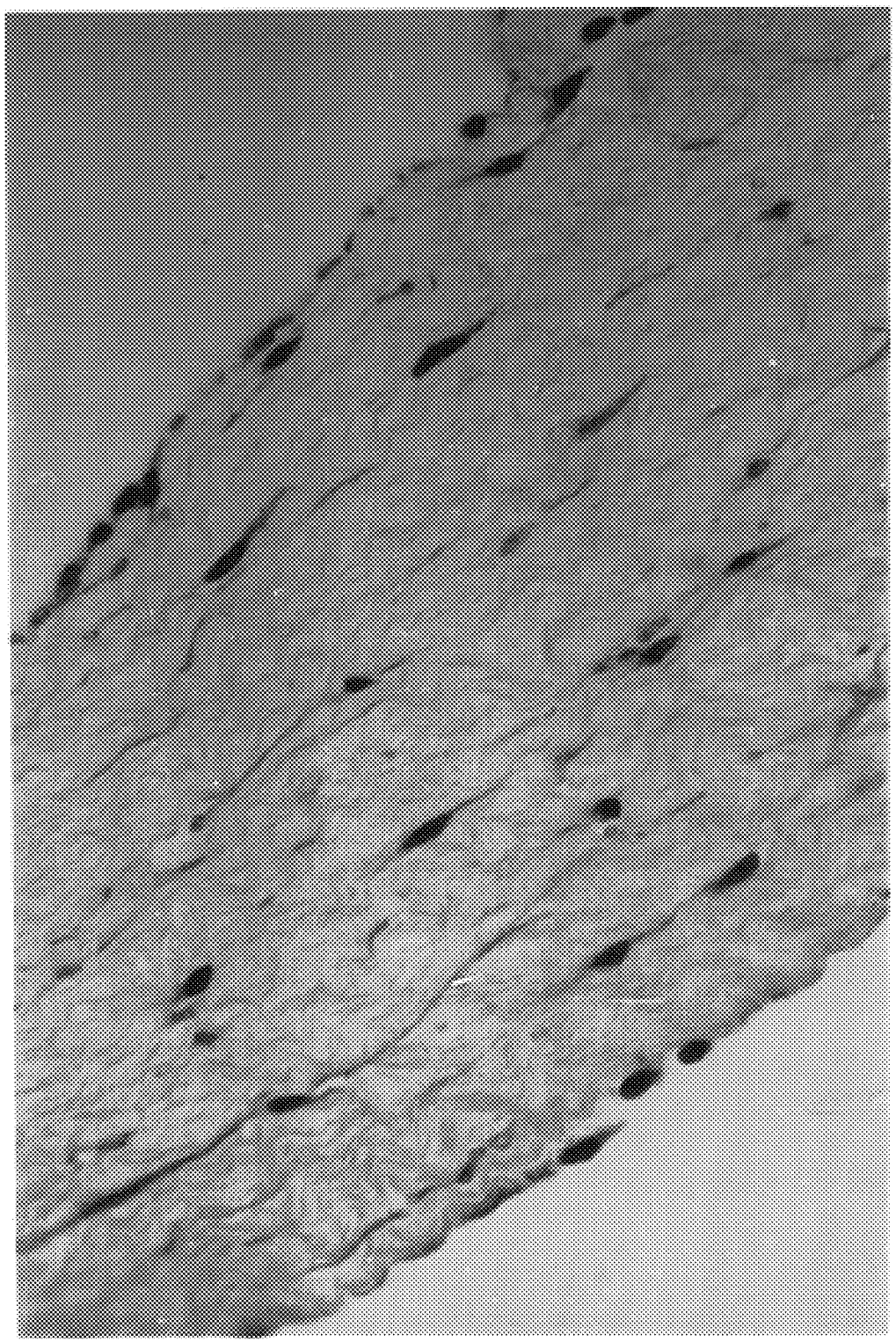
FIG. 1 is a photomicrograph of a cross section of the dermal tissue equivalent stained with hematoxylin and eosin and photographed at a magnification of 100×.

The nutrient and ionic composition of the culture medium is important to optimum control of the cell proliferation and the absence of contraction of the tissue equivalent. In one preferred embodiment, the culture medium is Ham's F-12 [1]medium supplemented with 6.0 g/L glucose, hereinafter "Modified Ham's F-12 Medium". Such a culture medium maintains the cellular component in a quiescent state with little cell proliferation, an essential requirement for the formation of a non-contracting tissue equivalent. In a preferred embodiment, the mitotic activity of the cellular component is maintained at a level corresponding to a mean population doubling time greater than 96 hours. In contrast, conventional culture media, such as Dulbecco's Modified Eagle Medium (DMEM)[2] (Table 1), produce a much shorter mean population doubling time of about 48 hours.

Several components of the culture medium are especially critical. The culture medium used in the initial formation of the tissue equivalents should not contain serum, i.e., it should be serum-free. It has been found that omitting serum avoids activating the cells to a proliferating and contracting phenotype.

The preferred culture medium, in addition to being serum-free, is relatively low in calcium, in a particularly preferred embodiment having about one-sixth the concentration of $CaCl_2$ found in DMEM. It has been found that relatively high levels of calcium initiate contraction of the tissue equivalents. Accordingly, the nutrient medium preferably contains no more than about 2 mM of calcium, preferably about 0.3 mM of calcium.

Several other components of the culture medium are important for the support of collagen synthesis by the cellular component of the tissue equivalent. The addition of ascorbate, α-ketoglutarate and glycine is important to assure mild stimulation of collagen synthesis. A preferred concentration of ascorbate is about 50 µg/ml. A preferred concentration of α-ketoglutarate is about 50 µg/ml. A preferred glycine concentration in the culture medium is about 27 mg/ml. The culture medium also contains about 2.7 grams/liter of additional glucose.

A preferred non-cellular component of the non-contracting tissue equivalent is collagen I. Most living connective tissues are composed of collagen I and collagen III in ratios which reflect an age dependent decrease in collagen III and an increase in collagen I. Although an ideal construction of the human connective tissue equivalent utilizes a mixture of human collagen I and collagen Imi, the cost of this is prohibitively expensive for most purposes. It has been discovered that acid solubilized bovine (calf) skin collagen I, at a concentration of approximately 3 to 5 mg of collagen per ml of HCl or Acetic acid, serves well and is far less expensive. The use of collagen I as the non-cellular component provides an economical and preferred embodiment of the present invention.

The finished form of the non-contracting tissue equivalent depends on the particular intended use. If the equivalents are to be used to assess the effects of alteration of the tissue environment such as the topical addition of a prospective drug or cosmetic material (e.g., a sunscreen) the material can be cast on semipermeable membrane inserts. Semipermeable cell culture inserts are plastic cups containing a mounted semipermeable membrane which can be made of collagen I, polycarbonate, mixed cellulose esters, hydrophilic PTFE, perfluorohydrocarbons, or alumina. Although the non-contracting tissue equivalent can be grown on any of these, preferred inserts are translucent inserts which do not interfere with the translucence of the non-contracting tissue equivalent. A particularly preferred translucent insert is the Millicell® CM hydrophilic PTFE insert (Millipore Corporation, Bedford, Mass. 01730). Most of the inserts are commercially available in two sizes to fit six well plates and 24 well plates (Corning or Falcon). After addition of the test compound, a variety of in situ tests can be conducted.

EXAMPLE 1

Construction of the Dermal Equivalent, a Basic Non-Contracting Tissue Equivalent The construction of a simple non-contracting tissue equivalent with a cellular component primarily comprising fibroblasts produces a dermal equivalent. The dermal equivalent is useful in itself for several purposes, as well as providing the basic foundation for the more complex non-contracting tissue equivalents that are discussed below.

The cells used in the non-contracting tissue equivalent were normal cells of mesenchymal origin such as fibroblasts obtained in primary culture as outgrowths from explanted tissues such as dermis or corneal stroma. The primary culture cells emerged from explanted tissue about a week to ten days after initiation of incubation. Both primary culture and expansion of cell number by subculturing is carried out in a medium, such as DMEM (Table 1), that supports rapid cell replication. The cells are subcultured at a split ratio of 1:3, are used in early passages (up to passage 5), and although they may be from donors of any age, cells from donors up to the age of about 30 are preferred. Dermal fibroblasts can be obtained from several sources, including skin tissue from circumcisions, breast and abdominal reductions. Ocular fibroblasts can be obtained from several sources, including corneal stroma subepithelium.

TABLE 1

Comparison of Ham's F-12 and DMEM

| Inorganic Salts: | DMEM (mg/L) | Ham's F-12 (mg/L) | Life Technologies 11320 (mg/L) |
|---|---|---|---|
| $CaCl_2$ (anhyd.) | 200.0 | 33.20 | 116.6 |
| $CuSO_4.5H_2O$ | — | 0.0025 | 0.0013 |
| $Fe(NO_3)_3.9H_2O$ | 0.10 | — | 0.05 |
| $FeSO_4.7H_2O$ | — | 0.83 | 0.417 |
| KCl | 400.00 | 223.60 | 311.80 |
| $MgCl_2$ (anhyd.) | — | 57.22 | 28.64 |
| $MgSO_4$ | 97.67 | — | 48.84 |
| NaCl | 6400.00 | 7599.00 | 6999.50 |
| $NaHCO_3$ | — | — | 2438.00 |
| $NaH_2PO_4.H_2O$ | 125.00 | — | 62.5 |
| $Na_2HPO_4$ (anhyd.) | — | 142.00 | 71.02 |
| $ZnSO_4.7H_2O$ | — | 0.86 | 0.432 |
| Other Components: | | | |
| D-Glucose | 4500.00 | 1802.00 | 3151.00 |
| Na hypoxanthine | — | 4.77 | 2.39 |
| Linoleic acid | — | 0.08 | 0.042 |
| Lipoic acid | — | 0.21 | 0.105 |
| Phenol Red | 15.0 | 1.20 | 8.10 |
| Putrescine.2HCl | — | 0.161 | 0.081 |
| Sodium pyruvate | 110.0 | 110.00 | 55.00 |
| Thymidine | — | 0.70 | — |
| Amino Acids: | | | |
| L-Alanine | — | 8.90 | 4.45 |
| L-Arginine.HCl | 84.00 | 211.00 | 147.50 |
| $L\text{-Asparagine.}H_2O$ | — | 15.00 | 7.50 |
| L-Aspartic acid | — | 13.00 | 6.65 |
| $L\text{-Cysteine.HCl.}H_2O$ | — | 35.00 | 17.56 |
| L-Cystine.2 HCl | 63.00 | — | 31.29 |
| L-Glutamic acid | — | 14.7 | 7.35 |
| L-Glutamine | 584.00 | 146.00 | 365.0 |
| Glycine | 30.00 | 7.50 | 18.75 |
| $L\text{-Histidine.HCl.}H_2O$ | 42.00 | 21.0 | 31.48 |
| L-Isoleucine | 105.00 | 4.00 | 54.47 |
| L-Leucine | 105.00 | 13.00 | 59.05 |
| L-Lysine.HCl | 146.00 | 36.50 | 91.25 |
| L-Methionine | 30.00 | 4.50 | 17.24 |
| L-Phenylalanine | 66.00 | 5.00 | 35.48 |
| L-Proline | — | 34.50 | 17.25 |
| L-Serine | 42.00 | 10.5 | 26.25 |
| L-Threonine | 95.00 | 12.00 | 53.45 |
| L-Tryptophan | 16.00 | 2.00 | 9.02 |
| $L\text{-Tyrosine.2Na.2}H_2O$ | 104.00 | 7.80 | 55.79 |
| L-Valine | 94.00 | 11.70 | 52.85 |
| Vitamins: | | | |
| Biotin | — | 0.007 | 0.0035 |
| D-Ca Pantothenate | 4.00 | 0.50 | 2.24 |
| Choline Chloride | 4.00 | 14.00 | 8.98 |
| Folic Acid | 4.00 | 1.30 | 2.65 |
| i-Inositol | 7.20 | 18.00 | 12.60 |
| Niacinamide | 4.00 | 0.04 | 2.02 |
| Pyridoxal.HCl | — | — | 2.0 |
| Pyridoxine.HCl | 4.00 | 0.06 | 0.031 |
| Riboflavin | 0.40 | 0.04 | 0.219 |
| Thiamine.HCl | 4.00 | 0.30 | 2.17 |
| Thymidine | — | — | 0.365 |
| Vitamin $B_{12}$ | — | 1.40 | 0.68 |

Human cells were isolated from normal human skin tissue pieces obtained as infant foreskins, or remnants from breast or abdominal reduction surgery. While the embodiments of the invention herein described comprise human cells, one skilled in the art would understand that the same procedures can be used, with minor modifications if necessary, for the construction of similar non-contracting tissue equivalents employing cells from other species.

The human skin tissue pieces were decontaminated by sequential incubation at room temperature in a 20% dilution of penicillin/streptomycin mixture (Sigma Chemical Company, St. Louis Mo.) dissolved in DMEM containing 10% fetal bovine serum (FBS) for at least twenty minutes followed by an additional 40 minutes incubation in 10% penicillin/streptomycin mix (10,000 U/ml penicillin+10 mg/ml streptomycin in 0.9% NaCl) dissolved in DMEM containing 10% FBS.

The decontaminated skin tissue pieces were then rinsed in sterile phosphate buffered saline (PBS, pH 7.4) and dissected to remove subcutaneous fat and connective tissue, leaving pieces about 2 mm to about 3 mm thick.

The dissected skin tissue pieces were then rinsed again in sterile PBS and then submerged in a solution of dispase (a neutral protease produced by *Bacillus polymyxa*), commercially available from Collaborative Biomedical Products, Two Oak Park, Bedford, Mass. 01730, diluted to 10 units/ml in keratinocyte growth medium (KGM, Clonetics/BioWhitaker, San Diego Calif.). KGM is a proprietary modification of MCDB 153 (Boyce, S. T. and Ham, R. G., J. Invest. Dermatology 81(Suppl.): 33s–40s (1983)), which is itself a modification of MCDB 152 (Tsao, M. C., et al., J. Cellular Physiology 110: 219–229 (1982)).

The dissected tissue pieces were incubated for at least 24 hours, preferably for at least 48 hours, at 4 degrees Celsius. The dispase-treated skin pieces were rinsed in sterile PBS, the epidermis was grasped at its edge with fine forceps and peeled off.

The removed epidermis pieces were placed in a 15 ml centrifuge tube and incubated with frequent agitation and vortexing in at least 5 ml of a trypsin/EDTA solution (0.05% trypsin in 0.53 mM EDTA tetrasodium salt, from Life Technologies, Grand Island, N.Y.) for 30 minutes at 37 degrees Celsius. This procedure separated desired basal and suprabasal cells in an epidermal cell suspension from the pieces of *stratum corneum*, which are resistant to digestion and float to the surface of the trypsin solution. The basal cells are the primary proliferative cell population isolated by this procedure.

At least 10 ml (twice the volume of trypsin solution used) of trypsin inhibitor solution (soybean trypsin inhibitor from Sigma Chemical Company, St. Louis, Mo.; at a concentration of 0.5 mg/ml; activity: 1 mg inhibits 1.7 mg of trypsin with an activity of 10,000 BAEE units/mg of protein) was added to the centrifuge tube and centrifuged at 3–6,000 rpm for about three minutes at room temperature to pellet the epidermal cells. The supernatant and pieces of *stratum corneum* were discarded.

Fresh DMEM plus 10% FBS was added to the centrifuge tube, and the pellet of epidermal cells was dissociated by repeated trituration using a syringe fitted with a 22 gauge hypodermic needle. The epidermal cell suspension produced consisted of all types of epidermal cells, but keratinocytes and melanocytes predominated. The epidermal cells obtained were transferred to tissue culture flasks at the desired density in the appropriate medium.

All plasticware and glassware used in cell culture (e.g., pipettes, centrifuge tubes, etc.), was precooled to 4 degrees Celsius, and all solutions were maintained at 4 degrees Celsius. A cold solution of acid solubilized collagen was mixed with cold reconstituted buffer (100 mM HEPES (N-[2-hydroxyethyl]piperazine-N'-[2-ethanesulfonic acid]) buffer, 25 mM $NaHCO_3$, 0.05M NaOH), and cold serum-free 10x Modified Ham's F-12 Medium in a ratio of 8:1:1, respectively. A suspension of fibroblasts (at least $1 \times 10^5$ cells per ml but preferably about $2.5 \times 10^5$ cells per ml) in a small volume of serum-free Modified Ham's F-12 Medium was then added to the mixture of acid solubilized collagen, buffer and medium and the cells were dispersed thoroughly in the cold viscous solution to form a suspension of collagen and cells. Aliquots of this suspension of collagen and cells were then pipetted into the desired casting forms, typically tissue culture dishes, such as a multiwell culture plate or semipermeable membrane cell culture inserts. The casting forms containing the suspension of collagen and cells were then transferred to an incubator at 37 degrees Celsius where gelation of the collagen took place.

Additional Modified Ham's F-12 Medium containing 5% FBS was added to the tissue culture dishes containing the formed translucent tissue equivalents after twelve hours. Within 24 hours the fibroblasts were observed to adopt their familiar quiescent elongated morphology (FIG. 1). The viability of the cultured non-contracting connecting tissue equivalent can be maintained over a period of several months simply by replacing the culture medium with fresh medium every third day.

Figure 2:
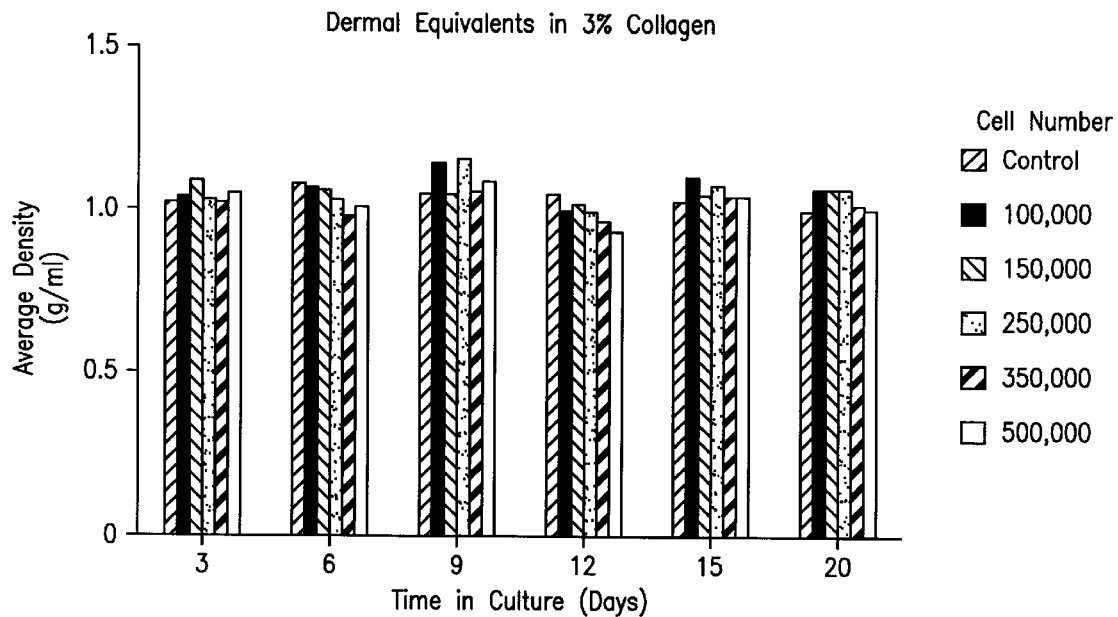
FIG. 2 is a histogram of data illustrating the substantially non-contracting quality of the connective tissue equivalent over a wide range of cell concentrations at a collagen content of 3%.
Figure 3:
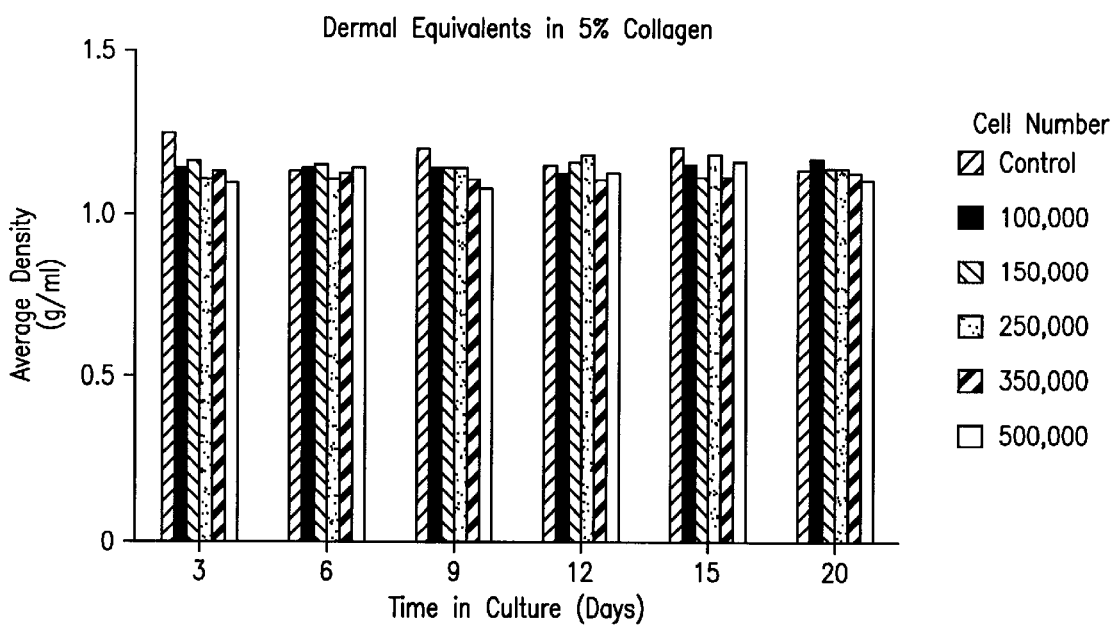
FIG. 3 is a histogram of data illustrating the substantially non-contracting quality of the connective tissue equivalent over a wide range of cell concentrations at a collagen content of 5%.

The tissue equivalents formed by this procedure were determined to be substantially non-contracting by measuring the density of tissue equivalents maintained for three weeks in Modified Ham's F-12 Medium. Relatively little change in density was observed (FIGS. 2 and 3 and Table 2).

TABLE 2

Dermal Equivalents Are Substantially Non-Contracting Density, g/ml and Relative density [% of Density at Three days in culture]

| Percent Collagen | Cells/ml | Day 3 | Day 6 | Day 9 | Day 12 | Day 15 | Day 20 |
|---|---|---|---|---|---|---|---|
| 3% | 0 | 1.02 | 1.08 | 1.05 | 1.05 | 1.02 | 1.01 |
|  |  | [100] | [105] | [103] | [103] | [101] | [98] |
|  | $1.0 \times 10^5$ | 1.04 | 1.07 | 1.15 | 0.99 | 1.11 | 1.07 |
|  |  | [100] | [104] | [111] | [96] | [107] | [103] |
|  | $1.5 \times 10^5$ | 1.09 | 1.06 | 1.05 | 1.02 | 1.05 | 1.07 |
|  |  | [100] | [98] | [96] | [93] | [107] | [98] |
|  | $2.5 \times 10^5$ | 1.04 | 1.03 | 1.16 | 0.99 | 1.09 | 1.07 |
|  |  | [100] | [100] | [112] | [96] | [96] | [103] |
|  | $3.5 \times 10^5$ | 1.02 | 0.98 | 1.06 | 0.97 | 1.05 | 1.03 |
|  |  | [100] | [97] | [104] | [96] | [105] | [101] |
|  | $5.0 \times 10^5$ | 1.05 | 1.02 | 1.09 | 0.94 | 1.05 | 1.01 |
|  |  | [100] | [97] | [104] | [104] | [100] | [96] |
| 5% | 0 | 1.15 | 1.05 | 1.11 | 1.07 | 1.12 | 1.06 |
|  |  | [100] | [91] | [96] | [93] | [98] | [92] |
|  | $1.0 \times 10^5$ | 1.06 | 1.06 | 1.06 | 1.05 | 1.07 | 1.09 |
|  |  | [100] | [100] | [100] | [99] | [101] | [103] |
|  | $1.5 \times 10^5$ | 1.08 | 1.07 | 1.06 | 1.08 | 1.03 | 1.06 |
|  |  | [100] | [99] | [98] | [100] | [97] | [98] |
|  | $2.5 \times 10^5$ | 1.02 | 1.03 | 1.06 | 1.10 | 1.10 | 1.06 |
|  |  | [100] | [101] | [104] | [108] | [108] | [104] |
|  | $3.5 \times 10^5$ | 1.05 | 1.05 | 1.03 | 1.03 | 1.04 | 1.05 |
|  |  | [100] | [100] | [98] | [98] | [99] | [100] |
|  | $5.0 \times 10^5$ | 1.02 | 1.06 | 1.00 | 1.06 | 1.08 | 1.03 |
|  |  | [100] | [104] | [98] | [104] | [106] | [101] |

The observed increases in density, corresponding to a contraction of the tissue equivalent, ranged from about 3% (5% collagen, $1.0 \times 10^5$ cells/ml, Day 20) to about 12% (3% collagen, $2.5 \times 10^5$ cells/ml, Day 9). Since density changes are volume-based, the corresponding linear shrinkage is proportional to the cube root of the density, i.e., the density measure of shrinkage after seventeen days in culture corresponded to about 1.4% to about 2.3% change in linear dimensions such as diameter. "Substantially non-contracting" is thus defined as showing less than about 5% shrinkage in linear dimensions after six to seventeen days in culture. Preferably, non-contracting tissue equivalents show less than about 3% shrinkage in linear dimensions after six to seventeen days in culture. There was no clear trend observed that related shrinkage to collagen concentration or to cell density.

Figure 4A:
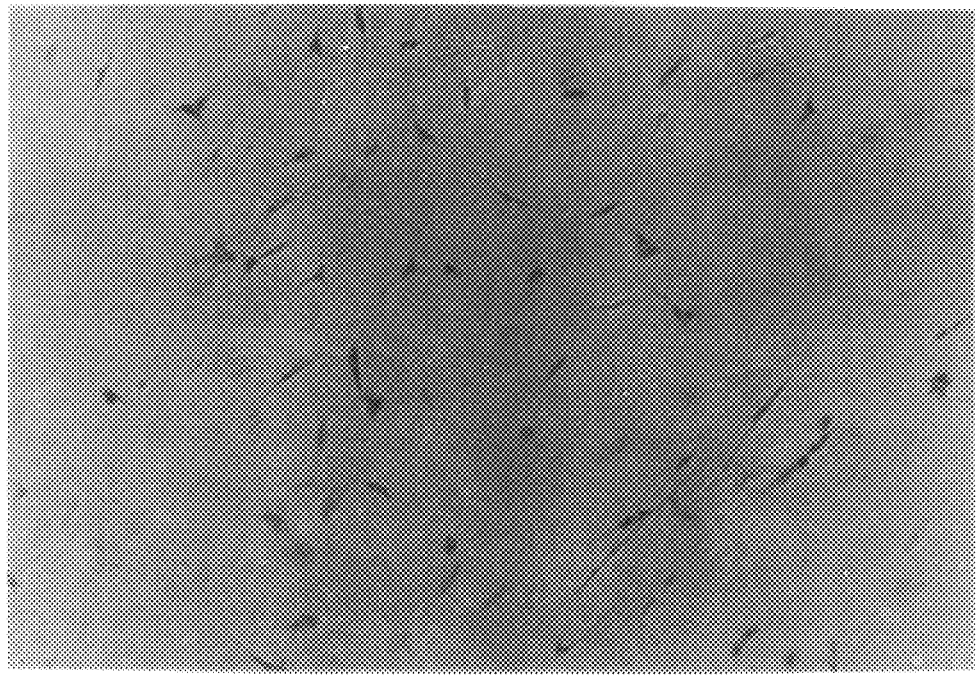
FIGS. 4A and 4B are photographs showing the translucent nature of the tissue equivalent viewed using an optical microscopic and transmitted light illumination, in which neutral red has been used to stain viable fibroblasts in the dermal equivalent.
Figure 4B:
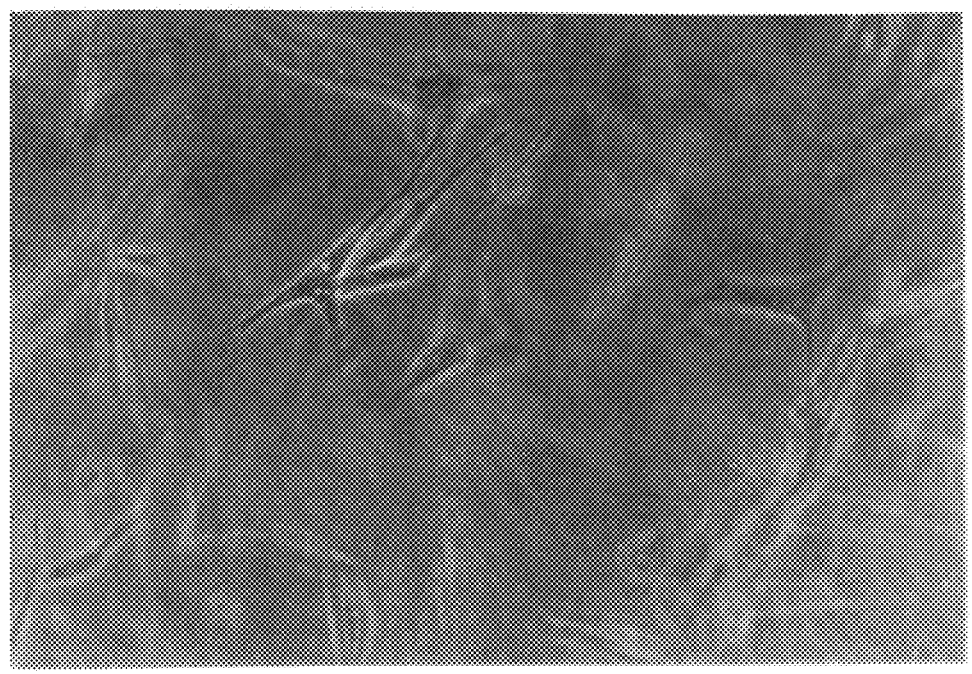

The produced non-contracting tissue equivalents were translucent, permitting the direct visual observation of the viability, morphology and other characteristics of the cellular component. FIG. 4 shows the typical appearance of non-contracting tissue equivalents in photomicrographs taken in the plane of the tissue equivalent. Viable fibroblasts stained with the vital dye neutral red are seen at low power, to show the distribution of cells within the tissue equivalent, and at high magnification, to show some details of cellular morphology.

Figure 5:
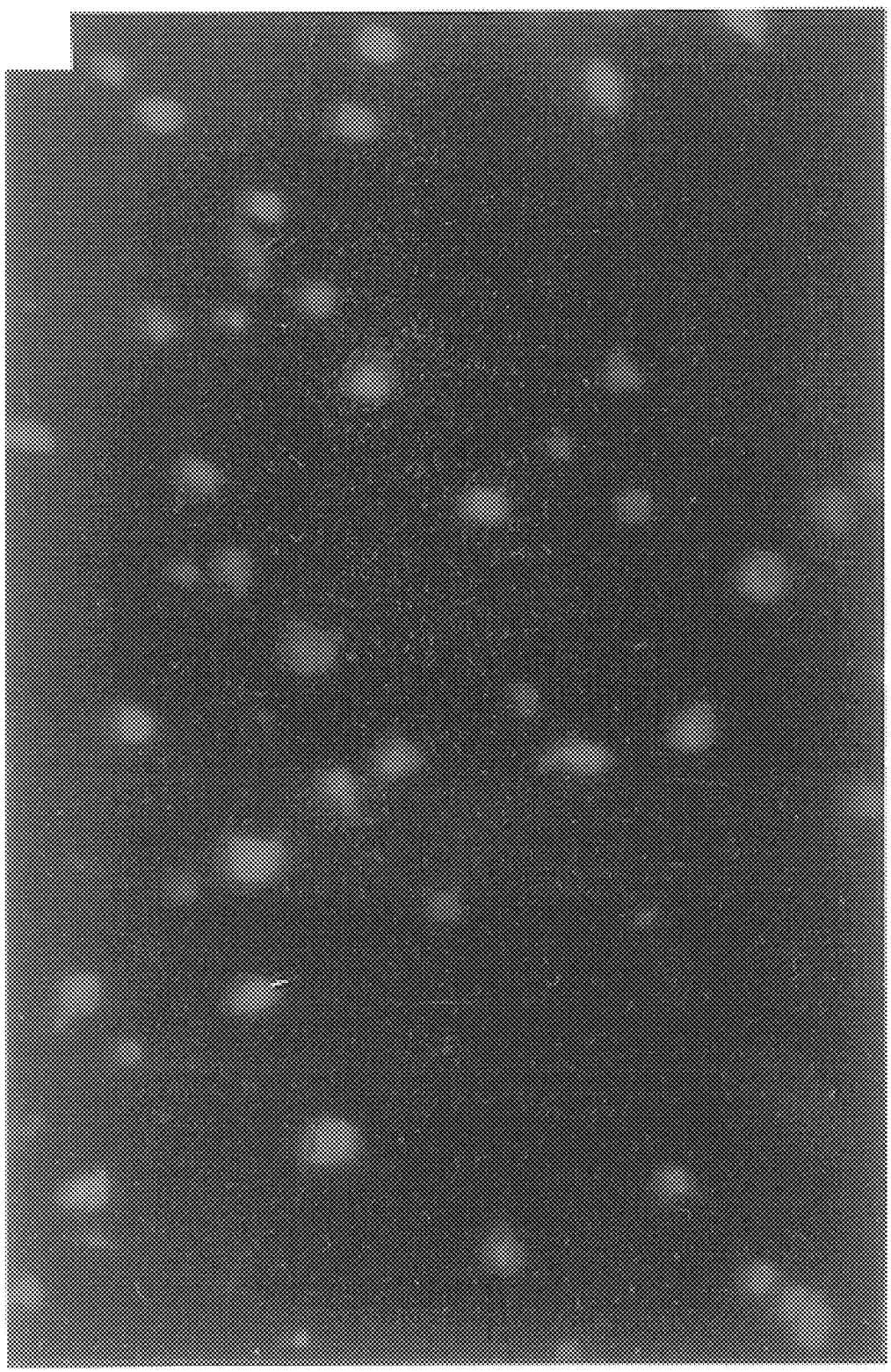
FIG. 5 is a photograph showing the utility of the translucent dermal equivalent in conjunction with fluorescent dyes, in this case labeled with CellTracker™ Orange, 5-(and 6-)-(((4-chloromethyl)benzyol)amino)-tetramethylrhodamine (Molecular Probes, Eugene, Oreg.) and photographed at a magnification of 100×.

The translucence of the non-contracting tissue equivalent also permits examination of the cellular component using fluorescence microscopy. FIG. 5 shows viable cells in a non-contracting tissue equivalent stained with another vital dye, CellTracker™ Orange, 5-(and 6-)-(((4-chloromethyl)benzyol)amino)-tetramethylrhodamine, (Molecular Probes, Eugene, Oreg.) and photographed at a magnification of 100×. The translucent characteristic of the non-contracting tissue equivalent is suitable for monitoring cellular morphology and cellular processes through the use of numerous other fluorescent dyes as well as fluorescent-labelled antibodies and oligonucleotides. The translucent characteristic of the non-contracting tissue equivalents of the present invention thus provides the ability to monitor expression of recombinant proteins by the cellular component using both standard transmitted light microscopy and fluorescence microscopy.

EXAMPLE 2

Bicellular Human Skin Equivalent

Dermal equivalents were constructed following the procedure of Example 1, using normal human dermal fibroblasts for the cellular component and collagen type I as the noncellular component. The dermal equivalents produced were used to support the attachment, growth and differentiation of normal human keratinocytes, thus forming bicellular human skin equivalents. The bicellular human skin equivalents thus formed are also substantially non-contracting, and are useful in applications needing a living in vitro model of human skin.

Dermal equivalents were cast as described in Example 1 in the wells of a multiwell plate. The cellular component was allowed to adapt to the collagenous matrix for a period of three days (but no more than about one week), during which time nutrients were provided by addition of Modified Ham's F-12 Medium containing no more than about 5% FBS. At the end of this adaptation period, the medium was removed from the top surface of the dermal equivalent. Collagen IV solution was then added to the surface of the dermal equivalent (12.5 $\mu g/cm^2$ of the dermal equivalent surface), neutralized with a neutralization buffer (same as for collagen I neutralization), and is allowed to permeate into the collagen I matrix at room temperature for 1 to 2 hours. The dermal equivalent so treated was the collagen IV used was derived from Engelbreth Holm-Swarm (EHS) lathrytic murine (mouse) tumor and obtained from Collaborative Biomedical Products, Bedford, Mass.

The number of keratinocytes seeded to the surface of the dermal equivalent depends upon the surface area. Also, the higher the seeding density the more quickly a monolayer of keratinocytes is established and the faster the air-liquid interface stage of the culture can be reached and initiation of differentiation then contacted with a suspension comprising normal human keratinocytes (80,000 to 250,000 cells depending on the surface area).

The resulting bicellular human skin equivalent was then covered with serum-free defined medium [Keratinocyte Growth Medium (KGM) containing no more than 0.1 mM calcium, preferably about 0.045 mM calcium]. The bicellular human skin equivalent was incubated overnight at 37 degrees Celsius to allow the keratinocytes to attach to the collagen IV layer. After this overnight incubation, the medium was changed to provide fresh KGM. The proliferation of the keratinocytes was monitored using phase contrast transmitted light microscopy until the cellular monolayer on the surface of the bicellular human skin equivalent becomes confluent. When the keratinocyte monolayer was confluent, the bicellular human skin equivalent was then removed carefully from the wells of the multiwell plate and placed on wire mesh grid or semipermeable membrane of a cell culture insert. The bicellular human skin equivalent was then elevated to air-liquid interface and maintained using KGM containing no more than 1.8 mM calcium, preferably 0.3 mM calcium, making sure that the surface of the culture was kept moist but not submerged. Differentiation of the bicellular human skin equivalent was then allowed to proceed with regular changes of medium provided about every two days. During this time the keratinocytes differentiated to form a stratified keratinized epithelium of the epidermis.

Figure 6A:
FIG. 6A is a cross section of the tissue equivalent after staining with hematoxylin and eosin as above and photographed at 100× magnification.
Figure 6B:
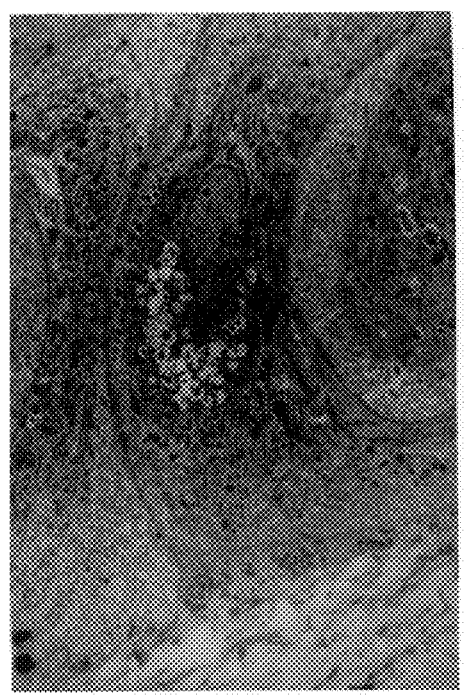
FIG. 6B is a transmission electron micrograph of the same human skin equivalent (photographed at 500× magnification) showing a columnar basal cell.
Figure 7A:
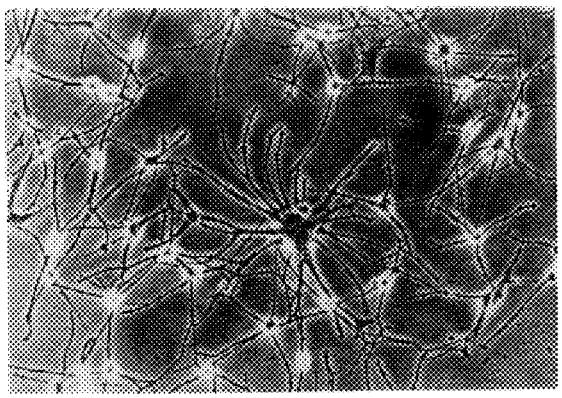
FIGS. 7A–7D are examples of the tricellular human skin equivalent containing fibroblasts, keratinocytes and melanocytes.
Figure 7B:
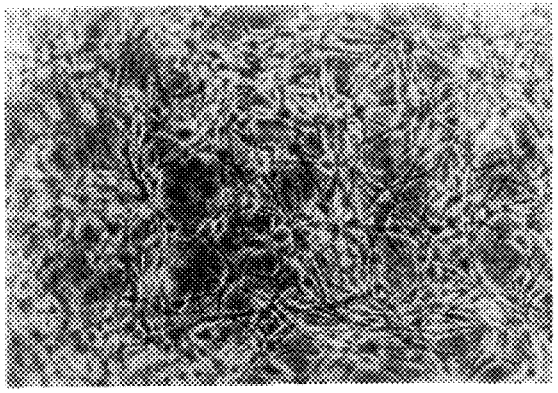
Figure 7C:
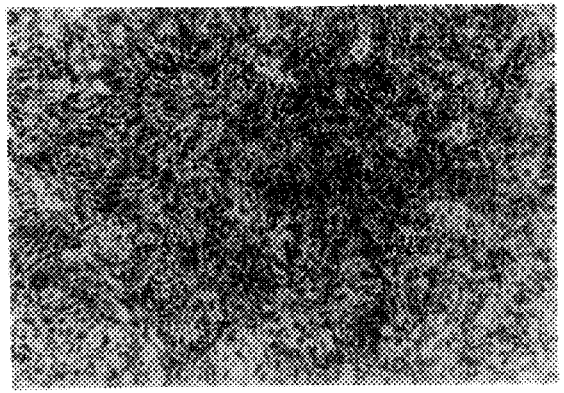
Figure 7D:
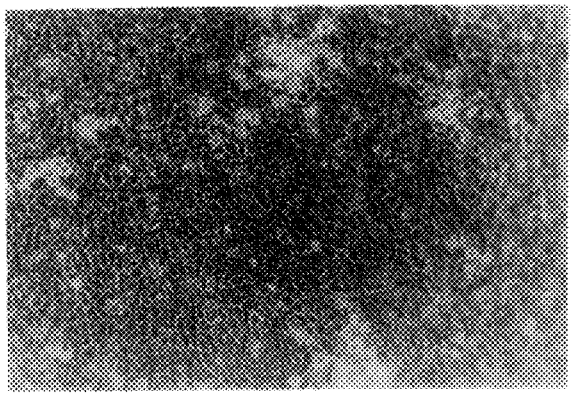

Histochemical analysis of bicellular human skin equivalents that had been fixed, embedded in paraffin and sectioned showed the presence of the layers typical of normal natural tissue, in addition to the basal layer of proliferating cells (FIG. 6). In FIG. 6, the dermal equivalent composed of collagen and fibroblasts can be seen as the lower layer, with proliferating basal cells (seen in detail in FIG. 6B) and other further differentiated cells comprising the epithelium, seen as darker successive upper layers. The cornified stratum corneum can be seen as the uppermost layer. The normal layers are clearly detectable: stratum spinosum (spinous layers), stratum granulosum (granular layers) and stratum corneum (the cornified layers). Thin sections of plastic-embedded bicellular human skin equivalents, examined using standard transmission electron microscopy, showed multiple tightly-packed layers of stratum corneum and numerous cell-cell junctions (desmosomes).

EXAMPLE 3

Alternative Procedure For Forming A Bicellular Human Skin Equivalent

In an alternative procedure, the dermal equivalent was cast in cell culture inserts located in the wells of a multiwell plate. In this format, the side of the dermal equivalent adjacent to the permeable bottom of the insert was thus established as the "systemic" side of the equivalent and the opposite surface of the equivalent was established as the "topical" side of the equivalent. The cellular component was allowed to adapt to the collagenous matrix for a period of about three days (but no more than about one week), during which time nutrients were provided by addition of modified Hams F-12 medium containing 5% FBS to both the insert and the well. At the end of this adaptation period, the medium bathing the top surface of the dermal equivalent was removed from insert, but not from the well. The top surface of the equivalent was then coated with collagen IV and contacted with a suspension of the keratinocytes as described in Example 2, above. The processes of cell attachment and formation of the keratinocyte monolayer were allowed to proceed in the presence of KGM as described above in Example 2. Thus, in this alternative procedure, each part of the bicellular skin equivalent was maintained in its own optimal medium.

When the keratinocyte monolayer was established, the KGM medium was removed from the upper ("topical") surface of the bicellular human skin equivalent and the surface was exposed to the air but was kept moist with the KGM containing at least 0.3 mM calcium. The modified Ham's F-12 medium in the well was replaced with KGM containing at no more than 1.8 mM calcium. The bicellular human skin equivalent was then allowed to differentiate for at least fourteen days.

EXAMPLE 4

Tricellular Human Skin Equivalent

The non-contracting dermal equivalent also supports the attachment and viability of epidermal melanocytes in the presence of growing and differentiating keratinocytes, thereby producing a tricellular human skin equivalent. The addition of melanocytes must be done prior to the introduction of keratinocytes, due to the different medium requirements of these cell types. Melanocyte attachment in vitro is more efficient in the presence of melanocyte growth medium (Melanocyte Growth Medium MGM3, Clonetics/BioWhittaker, San Diego, Calif. 92123). MGM3 does not support keratinocyte attachment and depletes their number by causing their terminal differentiation and detachment. Conversely, KGM does not support proliferation of melanocytes. The tricellular human skin equivalent was thus constructed by introducing melanocytes to the dermal equivalent before addition of the keratinocytes.

The dermal equivalent was formed as described in Example 1. After removal of the Modified Ham's F-12 Medium, the top surface of the dermal equivalent was coated with collagen type IV as described in Example 2. Then normal human melanocytes (8,000 to 25,000 cells depending on the surface area) dispersed in a serum-free defined medium (Melanocyte Growth Medium MGM3, Clonetics/BioWhittaker, San Diego, Calif. 92123) were applied and the combination was maintained in culture at 37 degrees Celsius for about 12–24 hours to allow for the attachment of the melanocytes. The dermal equivalent and attached melanocytes was rinsed with a small amount of serum-free KGM and then contacted with a suspension of keratinocytes in KGM containing no more than 0.1 mM calcium (70,000 to 225,000 depending on the area) as described above in Example 2.

The resulting tricellular human skin equivalent, with KGM containing no more than 0.1 mM calcium was incubated overnight at 37 degrees Celsius to allow the keratinocytes to attach. After this overnight incubation, the medium was changed to provide fresh KGM. The proliferation of the keratinocytes was monitored using phase contrast transmitted light microscopy until the cellular monolayer on the surface of the bicellular human skin equivalent becomes confluent. The equivalent was then cultured in Millicel inserts or on the wire mesh grid as described in Example 2 for at least about fourteen days to allow differentiation to proceed. The characterization of the tricellular human skin equivalent may be carried out in the same way as described for the bicellular skin equivalent in the Example 2, above.

The histological appearance of the tricellular human skin equivalent is shown in FIG. 7. FIG. 7(a) is a photomicrograph of a pure culture of melanocytes, original magnification 50×. FIG. 7(b) is a photomicrograph of a dermal equivalent with melanocytes, original magnification 25×. FIG. 7(c) is a photomicrograph of a dermal equivalent with melanocytes and keratinocytes, original magnification 25×. FIG. 7(d) is a photomicrograph of a dermal equivalent with keratinocytes, original magnification 25×.

EXAMPLE 5

Tricellular Human Skin Equivalent, Alternative Procedure In an alternative procedure, the dermal equivalent was cast in the cell culture inserts located in the wells of the multiwell plate as described in Example 3, above. In this format the lower surface of the dermal equivalent, facing the exterior of the insert, is established as the "systemic" side and the upper surface of the dermal equivalent as the "topical" side of the dermal equivalent. The cellular component was allowed to adapt to the collagenous matrix for a period of about three days (but no more than about one week), during which time nutrients were provided by addition of modified Hams F-12 medium containing 5% FBS to both the insert and the well. At the end of this adaptation period, the medium bathing the top surface of the dermal equivalent was removed from insert, but not from the well. The top surface of the equivalent was then coated with collagen IV and contacted with the melanocytes as described in Example 4 above. When the melanocytes were attached, the skin equivalent was contacted with a suspension of keratinocytes and the cell attachment and formation of the keratinocyte monolayer was allowed to proceed in the presence of KGM in the insert as described in Example 4. Thus each part of the skin equivalent was maintained in its own optimal medium. When the monolayer was established the KGM medium was removed from the surface of the equivalent. The upper ("topical") surface of the equivalent was exposed to the air but kept moist with the KGM containing at least 0.3 mM calcium. The modified Ham's F-12 medium in the well may be substituted with KGM containing no more than 1.8 mM calcium. The cellular component of the equivalent was then allowed to differentiate further for at least fourteen days. Using this alternative procedure it is not necessary to relocate the equivalent to the wire mesh grid. The characterization of the equivalent may be carried out in the same way as described for the bicellular skin equivalent in the Example 2 above.

EXAMPLE 6

Human Corneal Stroma Equivalent

The human corneal stroma equivalent was constructed using the same method as that described in Example 1 for the construction of the dermal equivalent, except that the cells used for the construction of the human corneal stroma equivalents were normal human corneal stroma fibroblasts-keratocytes.

Figure 8A:
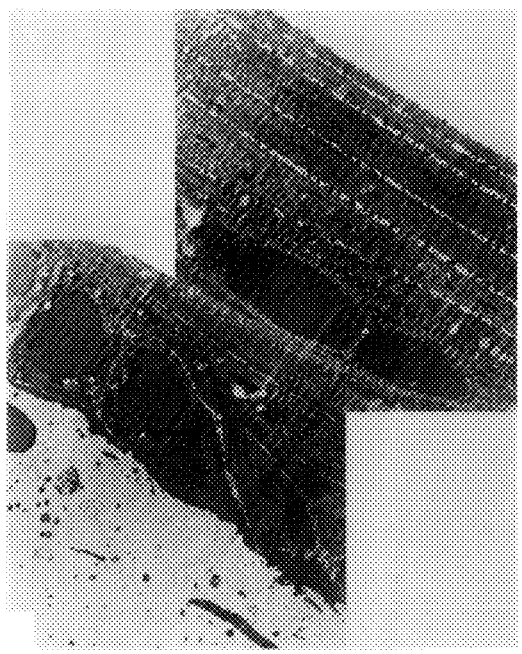
FIG. 8 shows a human corneal equivalent (a,b,d) formed using the non-contracting connective tissue equivalent showing epithelial morphology, compared to a normal human cornea (c,e)

To generate the human corneal epithelium equivalent, the corneal stroma equivalent was contacted with a suspension of normal human corneal epithelial cells. The method used is described above in Example 2; however, the method described in Example 3 is also suitable. Under these growth conditions at the air-liquid interface, the corneal epithelial cell differentiation was complete in about ten days and yielded a five to seven layer stratified non-keratinized epithelium (See FIG. 8a).

Figure 8B:
Figure 8C:
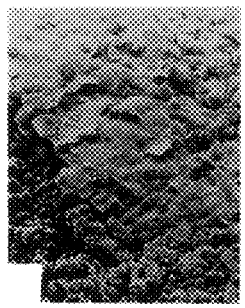
Figure 8D:
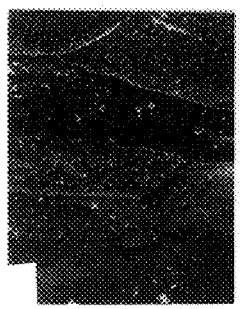
Figure 8E:

Examination of the fixed and osmicated surface of this epithelium by scanning electron microscopy (FIGS. 8b–8d) showed a surface morphology (high density of microvilli, and distinct cell borders) almost identical to the surface of a donor cornea (FIG. 8e).

Figure 9A:
FIGS. 9A–9F are a transmission electron micrograph of the epithelium of the human corneal equivalent showing normal structural elements of the cornea such as desmosomes, tight junctions, microvilli and microtubules.
Figure 9B:
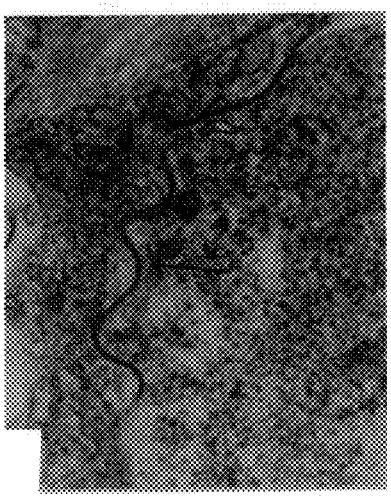
Figure 9C:
Figure 9D:
Figure 9E:
Figure 9F:

The examination of cross sections of the fixed and plastic embedded corneal epithelial equivalent by transmission electron microscopy showed a stratified epithelium of five to seven layers, composed of basal cuboidal cells and flattened supranasal wing cells. Throughout the layers are found typical cell-cell junctions such as desmosomes, tight junctions, and interdigitated tight junctions (FIGS. 9a–9d). The surface cells possessed numerous microvilli which at higher magnification show the projections of glycocalyx (FIG. 9e). Basal cells also showed the presence of microtubules and keratin fibers (FIG. 9f).

EXAMPLE 7

Human Corneal Endothelial Equivalent

The human corneal stroma equivalent was constructed as described in Example 6 using normal human corneal keratinocytes. After removal of the medium from the corneal stroma equivalent, the surface of the corneal stroma equivalent was coated with a mixture of fibronectin and collagen (FNC coating mix, catalog No. AF-10, Biological Research Faculty & Facility, Inc., Ijamsville, Md. 21754). The composition of the fibronectin and collagen mixture is given in Table 3, below.

TABLE 3

Fibronectin and Collagen Mixture

| Component | Concentration |
| --- | --- |
| Bovine Fibronectin | 10.0 µg/ml |
| Bovine Collagen, Type I | 35.0 µg/ml |
| Bovine Serum Albumin | 100.0 µg/ml |
| Potassium Chloride | 200.0 µg/ml |
| Phenol Red | 1.0 µg/ml |
| D-Glucose | 1.7 mg/ml |
| HEPES | 4.8 mg/ml |
| Sodium Chloride | 7.0 mg/ml |
| Sodium Phosphate (Monobasic) | 1.7 mg/ml |
| pH | 7.3–7.4 |
| Osmolality | 280–290 mOsm. |

The corneal stroma equivalent was contacted with a suspension of normal human corneal endothelial cells (early passage, preferably passage 1), at a cell density of 50,000/cm$^2$. The corneal stroma equivalent plus corneal endothelial cells was then covered with DMEM containing 10% FBS which was changed every two days, and the corneal endothelial cells were allowed to form a confluent monolayer.

Figure 10A:
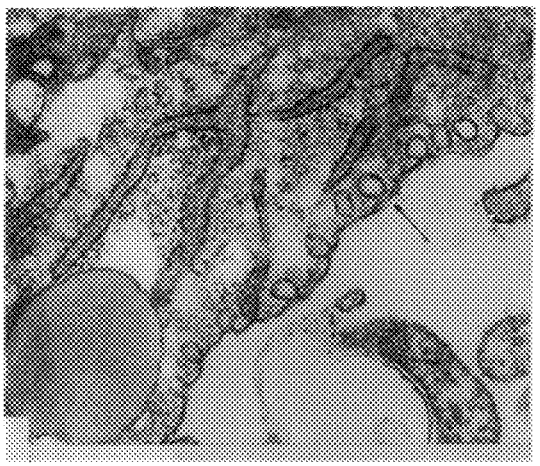
FIG. 10 is a photograph showing an example of the human corneal endothelium growing on the non-contracting translucent equivalent, showing the normal functional features of the endothelium including (a) caveolae, (b) coated pits, (c) microvilli, (d) basement membrane formation, (e) tight junctions and (f) desmosomes.
Figure 10D:
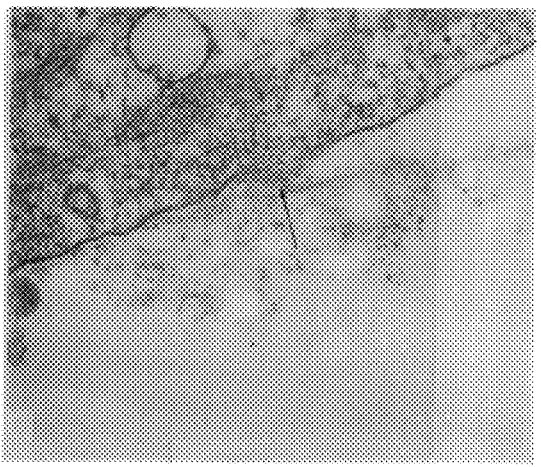
Figure 10B:
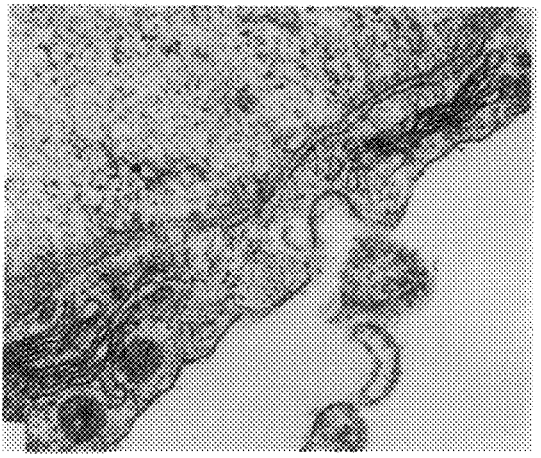
Figure 10E:
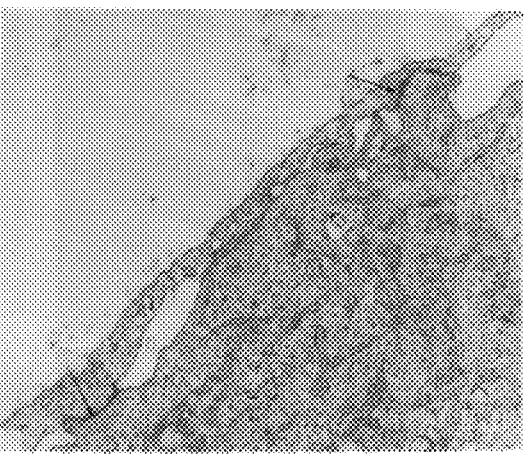
Figure 10C:
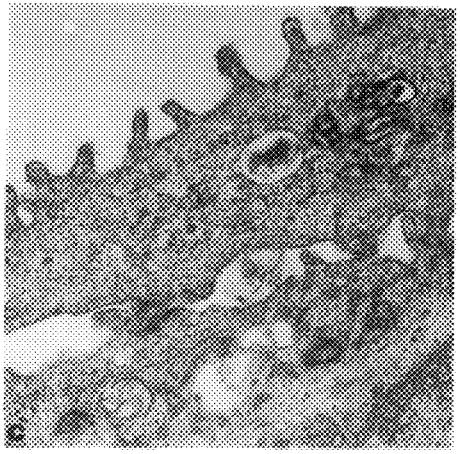
Figure 10F:
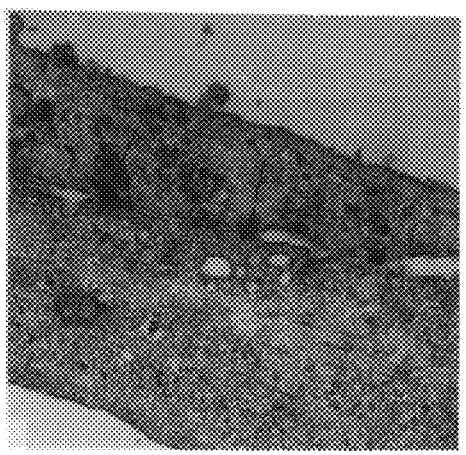

The resulting corneal endothelial equivalent was fixed, and either embedded in plastic and sectioned for transmission electron microscopic examination or, alternatively, fixed and osmicated for scanning electron microscopic examination. The transmission electron microscopy showed that the surface monolayer of cells added to the corneal stroma equivalent had the features typical of a functioning endothelium (see FIG. 10). The presence of caveolae (FIG. 10a), coated pits (FIG. 10b), microvilli (FIG. 10c), a basement membrane (FIG. 10d), and intercellular junctions (FIGS. 10e–f) was evident from the transmission electron micrographs. The scanning electron micrographs confirmed the presence of a monolayer which is rich in microvilli and distinct cell-cell borders. Immunofluorescence analysis of cross-sections obtained from paraffin embedded corneal endothelial equivalents showed the characteristic expression of cytokeratins 18 and 19.

In non-contracting tissue equivalents embodying the present invention, cell proliferation and differentiation can be stimulated, and collagen biosynthesis can be regulated, by hyperbaric oxygen at pressure levels up to about three atmospheres. Preferably, the exposure to hyperbaric oxygen is not continuous but effected periodically. That is, by subjecting the tissue equivalent, in the presence of an appropriate nutrient medium, to oxygen pressures of up to about 90 minutes daily over a time period of at least about two days, preferably about five to about 10 days. Oxygen pressures above about three atmospheres appear to be anti-mitotic to fibroblasts, thus during a hyperbaric oxygen treatment the oxygen pressure is not to exceed three atmospheres.

The following examples illustrate the effects of hyperbaric oxygen on tissue equivalents that embody the present invention.

EXAMPLE 8

Cell Culture

Human skin pieces (5 cm squares) were incubated at 4° C. in a solution of 20U/ml dispase (Collaborative Research; 5 mg collagen/cm2) in KGM (Keratinocyte Growth Medium, Clonetics Corp.), for 48 hours. The epidermis was separated from the dermis and dispersed in a solution containing 0.025% trypsin and 0.02% EDTA, by incubation at 37° C. and vigorous pipetting, to produce a single cell suspension. The resulting keratinocytes were then plated into tissue culture flasks coated with collagen VII, and cultured in KGM, a serum free defined medium at 37° C. (5% $CO_2$, 97% humidity). Dermal fibroblasts were obtained as outgrowths from explanted dermal tissue, after incubation at 37° C. 5% $CO_2$ 97% humidity) in DMEM containing 10% FBS. The cells were harvested with 0.05% trypsin, 0.02% EDTA, and passaged in their respective media or used for construction of dermal and skin equivalents. For experimental treatments the cells were plated into 25 cm tissue culture flasks (T-25), 6 well tissue culture (TC) plates (9.6 $cm^2$/well), or 4 well TC plates (2 $cm^2$/well).

EXAMPLE 9

Dermal Equivalents (DE)

Dermal equivalents were constructed at 4° C. by mixing 8 parts collagen (Type I acid solubilized, ICN Cellagen®; 3 mg/ml), 1 part of 10×Ham's F-12 medium, 1 part buffer (200 mM HEPES, 25 mM $Na_2CO_3$ and 50 mMN NaOH) and inoculating with dermal fibroblasts (1×105 cells/ml at 4° C.). For experimental treatments DE were cast in 4 or 12 well tissue culture plates and were maintained at 37° C. in Ham's F-12 Medium containing 5% FBS. Fibroblasts regained their normal morphology within 48 hours, after which DE were maintained in modified Ham's F-12 Medium, changing the media every 48 hours.

EXAMPLE 10

Human Skin Equivalents (HUSE)

Dermal equivalents, cast in 12 well tissue culture plates, were coated with collagen VII (Collaborative Research; 12 mg collagen/$cm^2$). Early passage keratinocytes (1.8× 105cells/$cm^2$), suspended in KGM (2 mls) were then plated onto DE. The medium was changed after 24 hours, and thereafter at 48 hour intervals. Once a confluent monolayer was formed, the DE were transferred to a wire mesh grids, elevated to the air-liquid interface, and the media was changed to modified KGM containing 1.8 mM $CaCl_2$; once lifted ("lift date" was "Day 0") the system was considered to be a "developing HUSE product". The "epidermis" remained at the air-liquid interface and differentiated for the duration of the experiment, the media being changed every 3 days. The HUSE product was considered mature after 14 days of differentiation.

EXAMPLE 11

Measurement of $pO_2$ in Culture Medium

A method similar to that described by Rafi et al., Am. J. Med. Genetics 61:299–303 (1966) was used to measure the partial pressure of oxygen ($pO_2$) dissolved in the culture medium bathing the cells. To each well of a multiwell tissue culture (TC) plate was added the appropriate culture medium to a depth of 2 mm. The TC plates were then placed in the treatment chamber, the chamber was flushed out with oxygen for five minutes and then pressurized over an additional five minute period. The pressure was maintained for 90 minutes after which time period the treatment chamber was decompressed over a period of five minutes. The TC plates were then removed from the chamber and the $pO_2$ measurement taken within two minutes using a polarographic oxygen electrode (Diamond General Development Corporation, Ann Arbor, Mich.). Dissolution of oxygen at four different pressures was measured in three different media. The observed data is summarized in Table 4 below, and represent a minimum of three replicate exposures at each oxygen pressure, and their means.

EXAMPLE 12

Hyperbaric Oxygen Treatments

The cells, DEs, or tissue equivalent products, contained in TC plates, were transferred into the treatment chamber, the lids were removed, and the TC plates covered with sterile gauze. The treatment chamber was sealed, the oxygen (100%) was blown through slowly to expel all the air (2 min.), and the chamber brought up to the appropriate pressure over a period of five minutes. The treatment pressure was maintained for 90 minutes. At the conclusion, decompression was carried out slowly over a five-minute period, and the treated cultures returned to the $CO_2$ incubator. The treatments were repeated for 2, 5, or 10 consecutive days, and a normal medium change schedule was maintained.

EXAMPLE 13

Neutral Red Viability Staining

The cells and equivalents were incubated in 1 ml of neutral red solution (1 mg/ml in appropriate media) for 4 hours at 37° C. The effects on the cells (fibroblasts/keratinocytes) were evaluated microscopically and photographically recorded. The entry of neutral red into the cells signified that they were viable. The observed results are presented in Table 5, below.

EXAMPLE 14

Dissolution of the DE

The DE were rinsed twice in PBS and incubated with collagenase solution {3 mg/ml Collagen I, Sigma, in 130 mM NaCl, 10 mM calcium acetate, 20 mM HEPES, pH 7.2} at 37° C. for 1 hr or until the matrix had dissolved. The cells were further dissociated with trypsin/EDTA (0.05%) as described above, sedimented by centrifugation and counted using a hemocytometer.

EXAMPLE 15

Collagen Synthesis Quantitation

Collagen production by near confluent monolayer of dermal fibroblasts was determined by measuring the incorporation of tritiated proline [3H-proline] into bacterial collagenase-sensitive protein [Postlethwaite et al., Proc. Nat. Acad. Sci. (USA) 75:871–875 (1978)] using an extensively modified method of Peterkofsky and Diegelmann, Developmental Biology 28:443–453 (1972). The wells of a six well TC plate (Falcon 3008) were seeded with $5\times10^5$ fibroblasts and were cultured in DMEM containing 5% FBS for 72 hr at 37° C. (humidified 5% $CO_2$ incubator). The medium was then replaced with serum free DMEM lacking in nonessential amino acids (500 ml), and containing 5 $\mu C$ L-proline[2, 3-3H] (20 Ci/mM, NEN, Boston, Mass.), and the hyperbaric treatments initiated. After 48 and 120 hours, two aliquots (200 ml) of culture supernatant were removed from each well. One aliquot was used to quantitate total protein production as follows: supernatant (200 ml) was added to 0.2 M Tris/0.3 M $CaCl_2$ buffer (pH 7.5, 70 ml), FBS (25 ml),N-ethylmaleimide (NEM, 30 ml), and a 0.75% solution of tannic acid (TA) in 50% trichloroacetic acid 9TCA) (75 ml). After 30 minutes incubation at 4° C., precipitated proteins were collected with suction onto a glass fiber filter (Reeve Angel Corp., Clifton, N.J.). The filters were washed with a cold 0.75% TA in 50% TCA (8 ml), and air dried (25° C., overnight). The filters, placed in scintillation vials containing 5 ml Aquasol (New England Nuclear), were chilled for 4 hr, and counted in a liquid scintillation counter.

The second aliquot of was used to quantitate the noncollagen protein as follows: supernatant (200 ml) was added to 0.2 M Tris/0.3 M $CaCl_2$ buffer (pH 7.5, 50 ml), NEM (30 ml) and bacterial collagenase (20 ml) (Worthington Biochemical Corp., Freehold, N.J.), purified just before use by gel filtration on Sephadex G-200 to remove proteinases. Supernatant with added collagenase was incubated at 37° C. for 90 min. After incubation, 20 ml FCS and 75 ml 50% TCA/0.75% tannic acid were added, and the sample was the non-collagen proteins allowed to precipitate for 30 minutes at 4° C. The precipitate was collected on glass fiber filters, and the radioactivity was measured by scintillation counting.

De novo synthesized collagen by each fibroblast culture was determined by substracting the noncollagen protein from the total proteins synthesized. Samples were assaved in quadruplicate or triplicate and the data are expressed as mean epm (+SEM) and/or percent of collagen produced relative to control cultures. (All column fractions were assayed in triplicate, and plotted points represent the average of the duplicate determinations). New collagen associated with the cell monolayer was not significant and is not reported.

EXAMPLE 16

Measurement of Oxygen Dissolved in The Medium

Oxygen levels in the culture medium were determined by measuring $pO_2$ levels at the end of each treatment with 100% oxygen using a method similar to that published by Rafi et al., supra. The results summarized in Table 4, below, show that under the experimental treatment conditions of increasing oxygen pressure in the treatment chamber, increasing levels of oxygen were dissolved in the culture medium. These levels were roughly a half of the partial pressure of oxygen gas applied to the medium. The extent of changes in the pH of the medium during the 90 min. treatment, were <0.10 pH unit and were considered insignificant.

TABLE 4

Relationship of Applied Oxygen Pressure and Measured $pO_2$ in a Culture

| CULTURE MEDIUM | APPLIED $O_2$ PRESSURE | MEASURED $pO_2$ (Mean of three readings) |
| --- | --- | --- |
| DMEM KBM KGM | 1 atm. - 760 mm Hg | 316 mm Hg |
| DMEM KBM KGM | 2 atm. - 1520 mm Hg | 800 mm Hg |
| DMEM KBM KGH | 2.5 atm. - 1900 mm Hg | 941 mm Hg |
| DMEM KBM KGM | 3 atm. - 2280 mm Hg | 1215 mm Hg |

DMEM - Dulbecco's Modified Eagle Media
KBM - Keratinocyte Basal Medium, Serum-Free
KGM - Keratinocyte Growth Medium, Serum-Free

Qualitative Effects of Hyperbaric Oxygen on Fibroblasts and Keratinocytes

Neutral red viability results derived after monolayer cultures of normal human skin fibroblasts and keratinocytes dermal equivalents (DEs) (submerged and at air-liquid interface), and tissue equivalent product, where exposed to several pressures of 100% oxygen are summarized in Table 5 below.

TABLE 5

Effects of Hyperbaric Oxygen

| TARGET | TREATMENT | GAS | PRESSURE (mm Hg) | OUTCOME |
| --- | --- | --- | --- | --- |
| Fibroblasts | Continuous 12 hrs | 100% $O_2$ | 760 | Non-Toxic |
|  |  |  | 1520 | Some Toxicity |
|  |  |  | 2280 | Some Toxicity |
| Fibroblasts | 3 hrs/day for 5 days | 100% $O_2$ | 760 | Non-Toxic |
|  |  |  | 320 | Non-Toxic |
|  |  |  | 480 | Non-Toxic |
| Keratinocytes | Continuous 12 hrs or 90 min/day for 10 days | 100% $O_2$ | 760 | Non-Toxic |
|  |  |  | 1520 | Non-Toxic |
|  |  |  | 2280 | Non-Toxic |
| Fibroblasts in Dermal Eq. on Grids | 90 min/day for 10 days | 100% $O_2$ | 760 | Non-Toxic |
|  |  |  | 1520 | Some Toxicity |
|  |  |  | 2280 | Some Toxicity |
| Fibroblasts in Dermal Eq. Submerged | 90 min/day for 10 days | 100% $O_2$ | 760 | Non-Toxic |
|  |  |  | 1520 | Non-Toxic |
|  |  |  | 2280 | Non-Toxic |
| HUSE Product | 90 min/day for 10 days | 100% $O_2$ | 760 | Non-Toxic |
|  |  |  | 1520 | Non-Toxic |
|  |  |  | 2280 | Non-Toxic |

When the fibroblasts were exposed to 100% oxygen some toxicity was observed only after continuous 12 hrs treatment at 2 and 3 atmospheres. Light microscopic examination of the monolayer cultures showed no changes in morphology as a result of sub-toxic hyperbaric oxygen (HBO) treatments. Fibroblasts showing toxicity exhibited morphological changes ranging from cell enlargement and extensive vacuolation to rounding and cell death confirmed by exclusion of neutral red. Cytotoxicity of fibroblasts in the non-submerged DEs, observed by light microscopy, was also evidenced by morphological changes such as cell rounding. Dead cells, whether round or shrunken, did not take up neutral red.

No toxicity was observed at any pressure when monolayer cultures of normal human keratinocytes were treated with 100% oxygen. Light microscopic examination of cultures treated continuously for up to 12 hours with 100% oxygen at 1 atmosphere, showed large numbers of cells which detached from the growing surface and were floating in the medium. The monolayer also showed considerable heterogeneity in cell size with a number of large, flat, differentiated keratinocytes, which remained attached to the growing surface. As was confirmed by neutral red uptake, all the cells including "the floaters" were viable. Monolayer cultures exposed to increasing partial pressures of oxygen and length of exposure (eg. 90 min./day 2 atm. for 10 days) showed increasing numbers of floating keratinocytes; in these cultures floating cells are continuously removed with the spent medium. Similarly developing HUSE products, which is a combination of submerged DE and keratinocytes were not adversely affected when treated with 100% oxygen up to 3 atmospheres.

EXAMPLE 17

Quantitative Effect of HBO on Fibroblast and Keratinocytes

Figure 11:
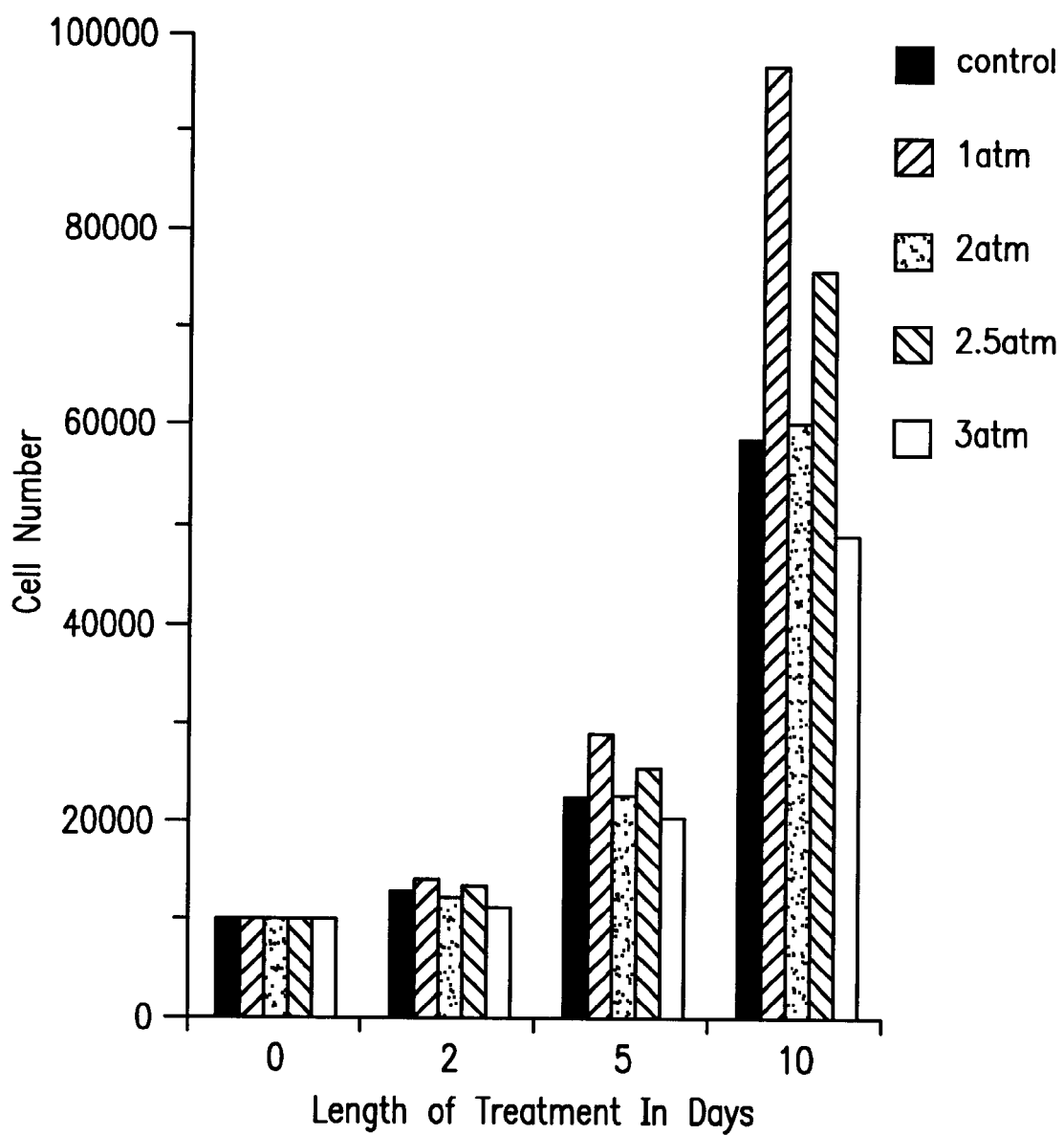
FIG. 11 is a histogram showing cell numbers after days of human fibroblast treatment at different pressure levels of oxygen.

Periodic treatment (90 min./day for ten days) of normal human dermal fibroblasts monolayers from a 17-year old donor with 100% oxygen at several pressures (1, 2, 2.5 and 3 atm.) is summarized in FIG. 11. These results shows that significant increase in cell numbers occurs after five days of treatment and that this effect is particularly pronounced after Day 10. Stimulation of cell proliferation was consistently observed at 1 and 2.5 atm. of 100% oxygen whereas treatment at 3 atm was consistently non-stimulating and perhaps marginally anti-mitotic.

Figure 12:
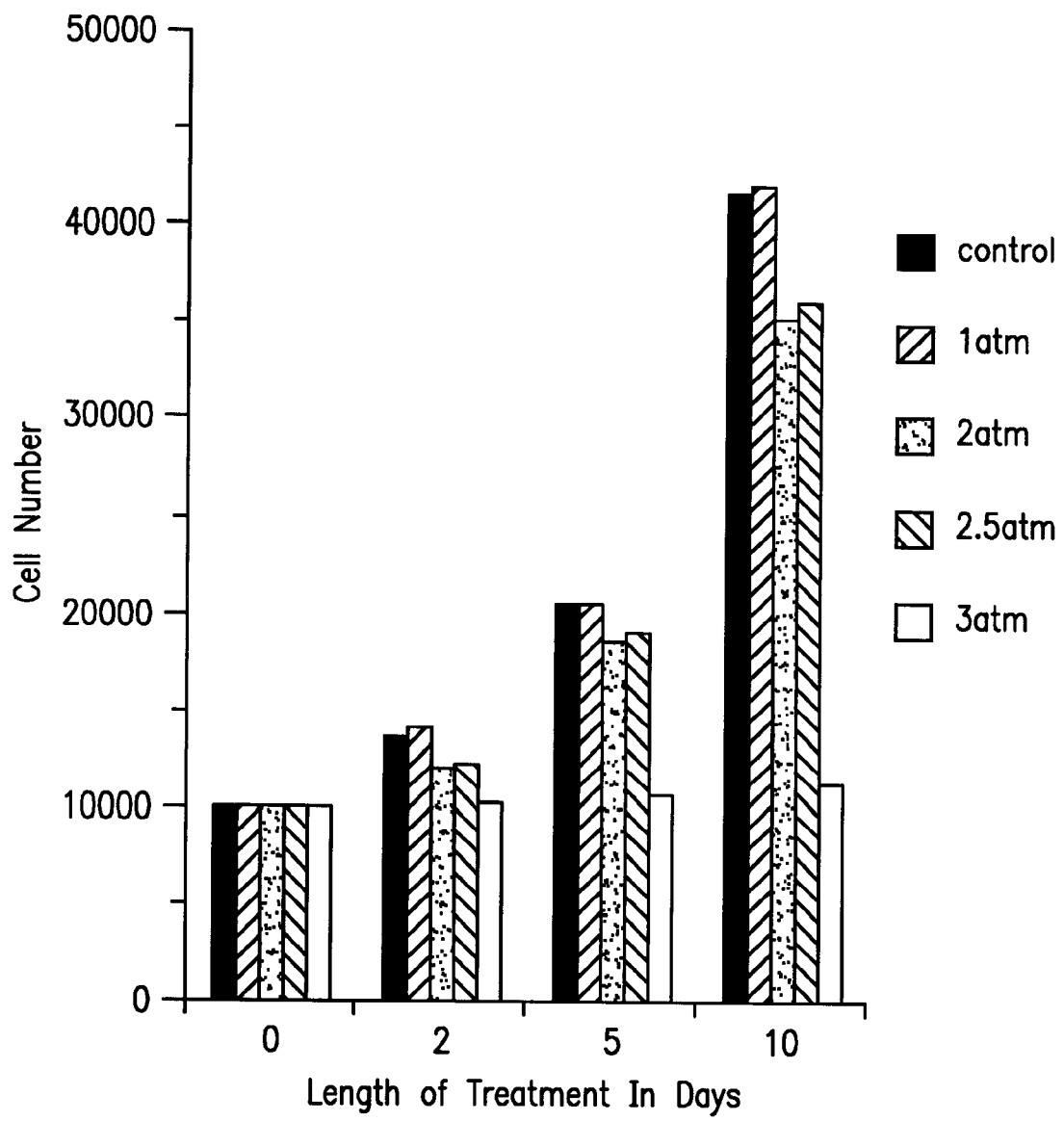
FIG. 12 is a histogram showing cell numbers after days of human keratinocyte treatment at different pressure levels of oxygen.

The results from a similar series of periodic HBO treatments of normal human keratinocyte monolayers, from the above donor, are summarized in FIG. 12. An increase in cell number throughout the treatment period, reaching a maximum at 10 days, is seen in the control cultures. This outcome is paralleled by the monolayer cultures treated at 1 atm. which were consistently indistinguishable from the controls. The results of the treatments at 2 and 2.5 atm. follow the same trend as the controls and 1 atm. treatments, but are not as mitotic as the latter. The notable exception is the treatment of keratinocyte monolayer at 3 atm. of 100% oxygen where a constant number of cells, well below the numbers obtained in other treatments, was harvested throughout the treatment period.

EXAMPLE 18

HBO Effect on Epidermopoiesis in a Skin Equivalent

A separate set of experiments was conducted to determine the effects of HBO on epidermopoiesis. In these experiments DEs, seeded with keratinocytes, were equilibrated for 48 hours and then subjected to HBO treatments 90 minutes/day for 10 (lays. Cross-sections of fixed and parafin embedded human skin equivalent product, obtained after 10 days of HBO treatment at 1 and 2 atm of 100% oxygen and untreated 10 day controls, were stained with hematoxylin and eosin. A progressive increase in epidermal thickness due to oxygen tension at 1 and 2 as compared with the untreated control was noted. Cornification of the epidermal layer in the human skin equivalent product was particularly stimulated by HBO.

EXAMPLE 19

Effect of HBO on Collagen Synthesis

Figure 13:
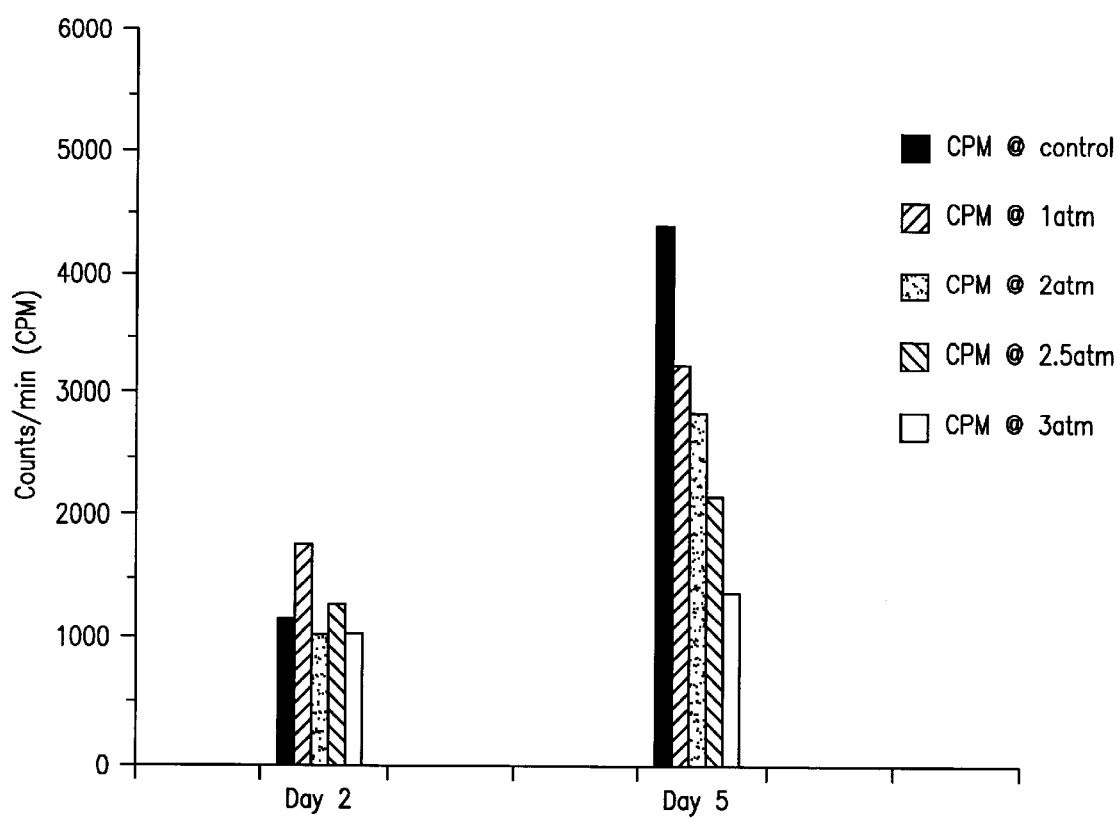
FIG. 13 is a histogram showing collagen synthesis by human dermal fibroblasts over 2-day and 5-day time periods in response to oxygen at various pressure levels.

Collagen synthesis by normal human dermal fibroblasts in response to exposure to 1, 2, 2.5 and 3 atmospheres of 100% oxygen was determined and compared with the response from the untreated controls. Collagen synthesis was quantitated by incorporation of tritiated proline. Newly synthesized collagen was deduced by subtracting the non-collagenous protein from the total protein synthesized over a period of 2 days and 5 days. FIG. 13 shows that collagen synthesis was elevated at 1 atmosphere 100% oxygen after two days of treatment. The levels of collagen synthesis were observed to be higher after five days of treatment than after two days for all pressure levels of 10% oxygen. However, with increased HBO there was an indication that inhibition of collagen synthesis under these conditions had taken place.

EXAMPLE 20

Following the methodology in Clark et al., *J. Clin. Invest.*, 84: 1036–1040 (1989), normal human infant foreskin fibroblasts were cultured in Eagle's MEM to a cell density of 1,000,000/ml. Each culture was seeded at 4° C. into collagen solution prepared as described by McPherson et al. *J. Biol. Chem.* 256: 11330–11336 (1981). The resulting matrices were poured into a 48 well plate at a volume of 0.5 ml per well (each well had an area of 16 square mnm). The wells of the plate were treated with BSA and media alone added as described in Clark et al. A total of 10 wells (hereinafter referred as the "Clark wells"; the terms "Clark wells" and "Clark matrices" are regarded as equivalent terms within Example 20), to provide ten repeats collectively referred to as Clark Run # 1, were generated using about 5 mnls of collagen and 5,000,000 cells. The observed data is summarized in Tables 6 to 20.

Fibroblast populated collagen matrices (dermal equivalents) were prepared and simultaneously added to a further ten wells in the same well plate (hereinafter referred as the "D&G wells"; the terms "D&G wells" and "D&G matrices" are regarded as equivalent terms within Example 20). The 48 well plate was maintained at 37° C. in a humidified $CO_2$ incubator to allow the Clark wells and the D&G wells to gel. Observations were made at time intervals as described below.

The experiment was repeated to provide a second set of Clark wells (Clark Run #2) and two sets of ten of D&G wells (D&G Run #2). In view of the problems discussed below, date was collected on only nine wells in the Clark #1 and Clark #2 Runs.

Observations:

After setup, the wells Dimitrijevich wells gelled within 10 to 15 minutes in Runs #1 and #2. In contrast, gelling times for the dermal equivalents in the Clark #1 and #2 runs were variable; about 250 $\mu$l of liquid were present on the surface of the Clark "gels" for as long as an hour after set up making it difficult to discern when the gelling was complete. The liquid present on the surface of the "gels" in the Clark runs made it difficult to monitor changes in the area (i.e. the contraction) of the Clark "gels" in Runs #1 and #2.

For example, meaningful inverted microscope examination of the matrices in the Clark wells proved difficult. Sedimentation of cells occurred in the Clark wells during the variable gelling period caused non-uniform distribution of cells in the Clark "gels". The sedimentation in the Clark wells caused some cells to emerge from the Clark "gels" resulting in inappropriate cell activity at the interface between the Clark "gels" and the plastic walls of the wells causing such cells to experience a different environment from that otherwise provided by the three dimensional environment of the Clark matrices. Hence, a disproportionate number of cells in the Clark wells were free to develop different characteristics from those still held in the Clark matrices. Sedimentation of cells did not occur in the D&G matrices resulting in a uniform environment and distribution of cells in the D&G gels.

Figures 14A, 14B, 14C, 14D:
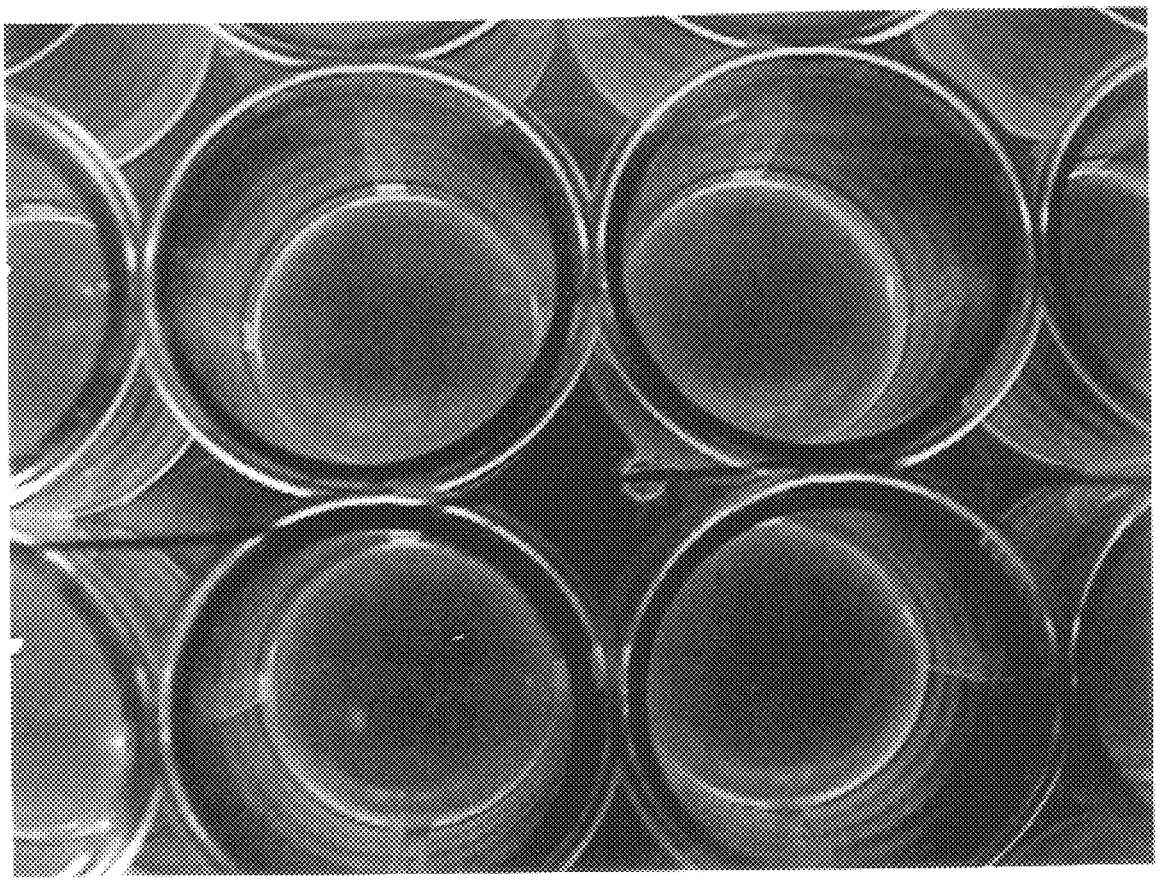
FIG. 14 is a photograph showing surface areas of two present gels (A and B) and two prior art gels (C and D) in Run #2 (Example 20) at 0 hours.
Figure 15:
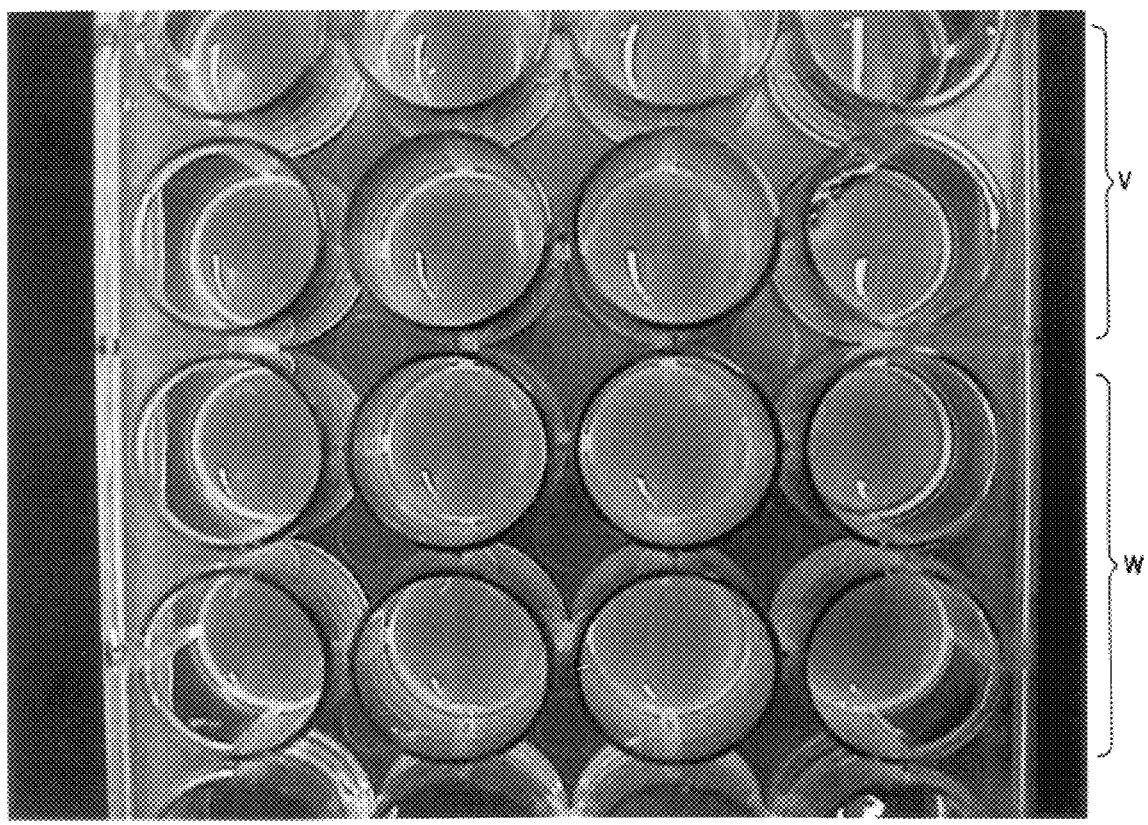
FIG. 15 is a photograph showing surface areas of two rows of present gels (marked as V) and two rows of prior art gels (W) in Run #2 (Example 20) at 0 hours.
Figure 16:
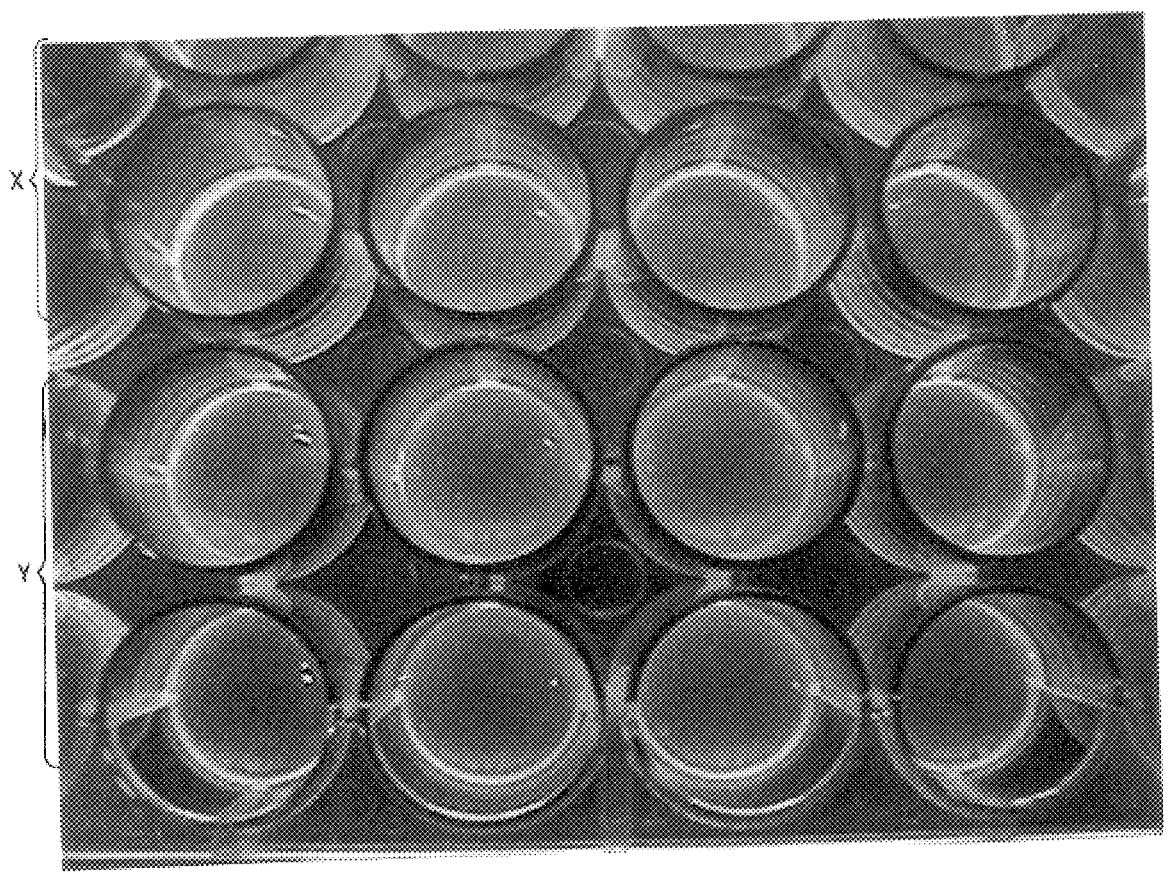
FIG. 16 is a photograph showing surface areas of two rows of present gels (X) and two rows of prior art gels (Y) in Run #2 (Example 20) at 20 minutes.

FIG. 14 is a photograph showing surface areas of two D&G gels (A and B) and two Clark gels (C and D) in Run #2 at 0 hours; FIG. 15 is a photograph showing surface areas of two rows (marked as V) of D&G gels and two rows of Clark gels (W) in run #2 at 0 hours; and FIG. 16 is a photograph showing surface areas of two rows (marked as X) of D&G gels and two rows of Clark gels (Y) in Run #2 at 20 minutes.

Figure 17:
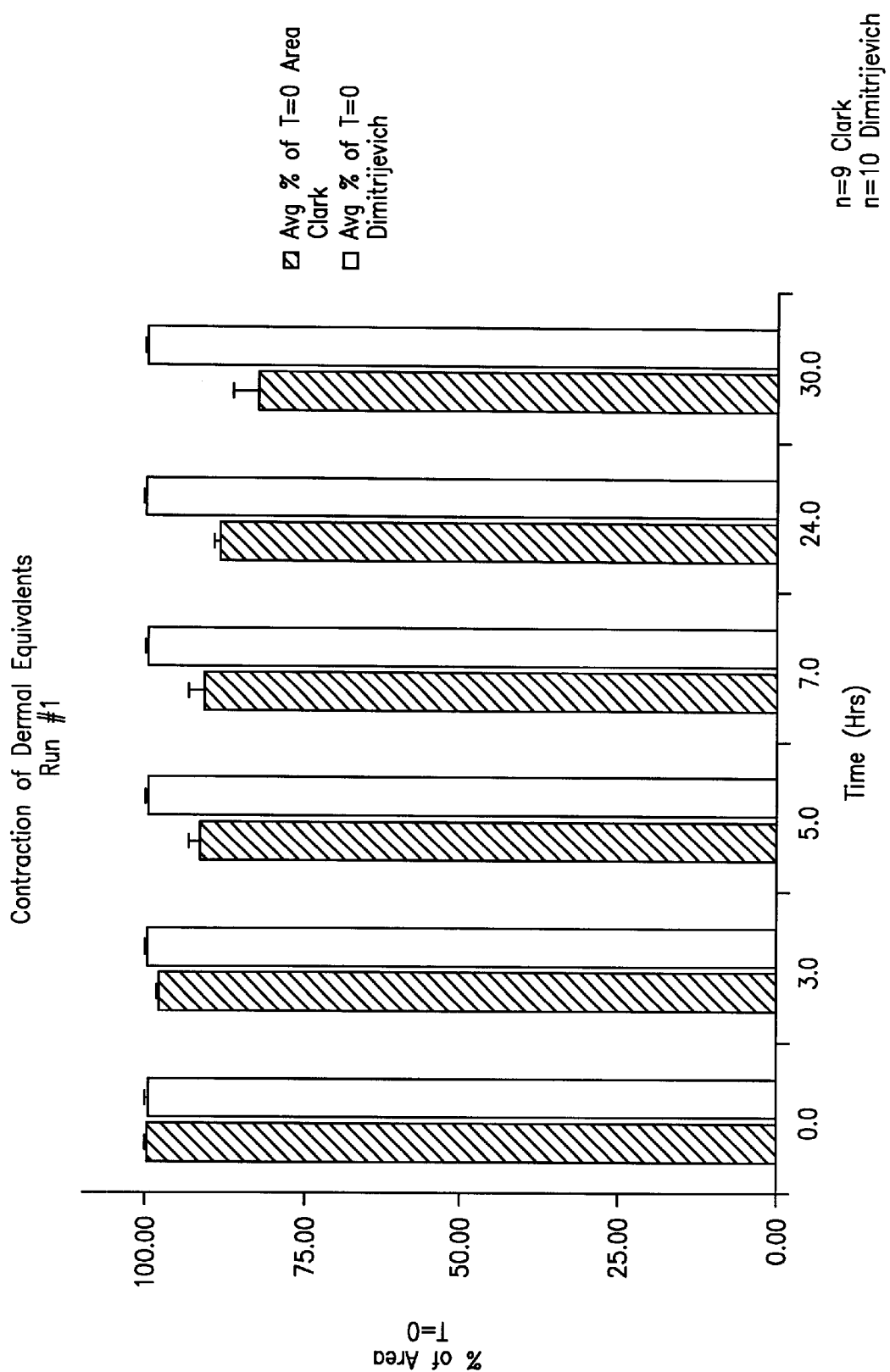
FIG. 17 is a histogram showing comparative surface area data for Run #1 (Example 20) over a 30-hour period.
Figure 18:
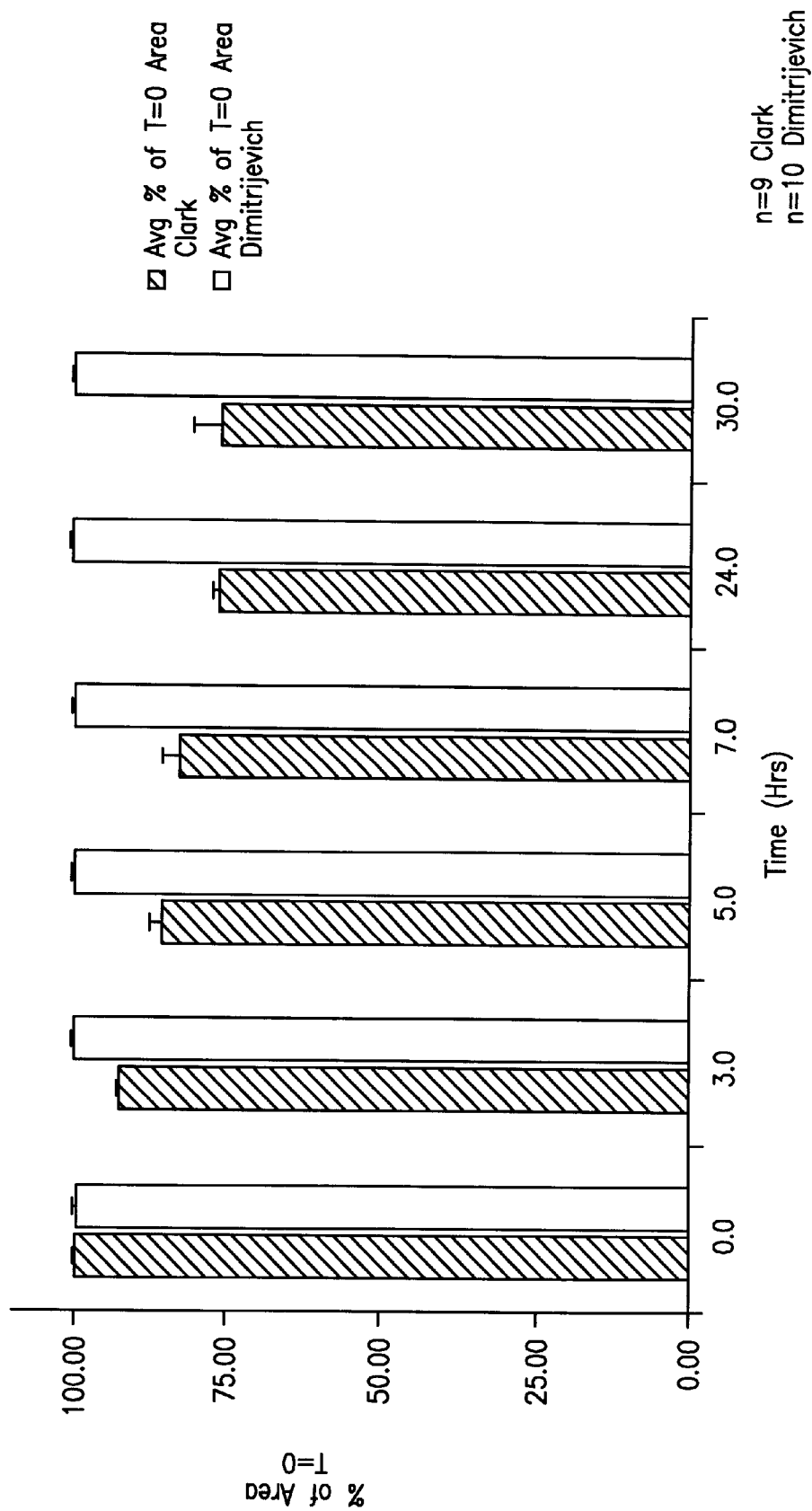
FIG. 18 is a histogram showing comparative surface area data for Run #2 (Example 20) over a 30-hour period.
Figure 19:
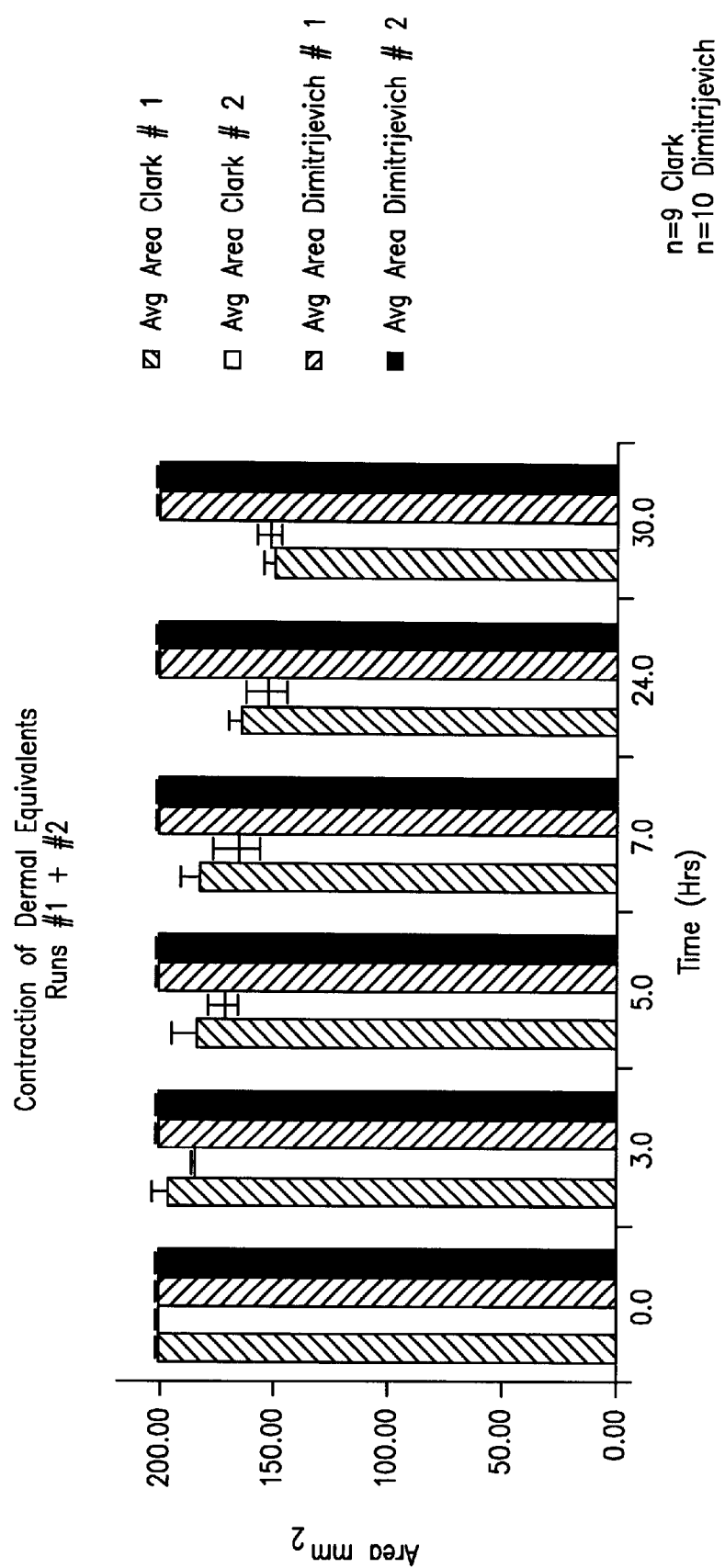
FIG. 19 is a histogram showing comparative surface area data for Runs #1 and #2 (Example 20) over a 30-hour period.
Figure 20:
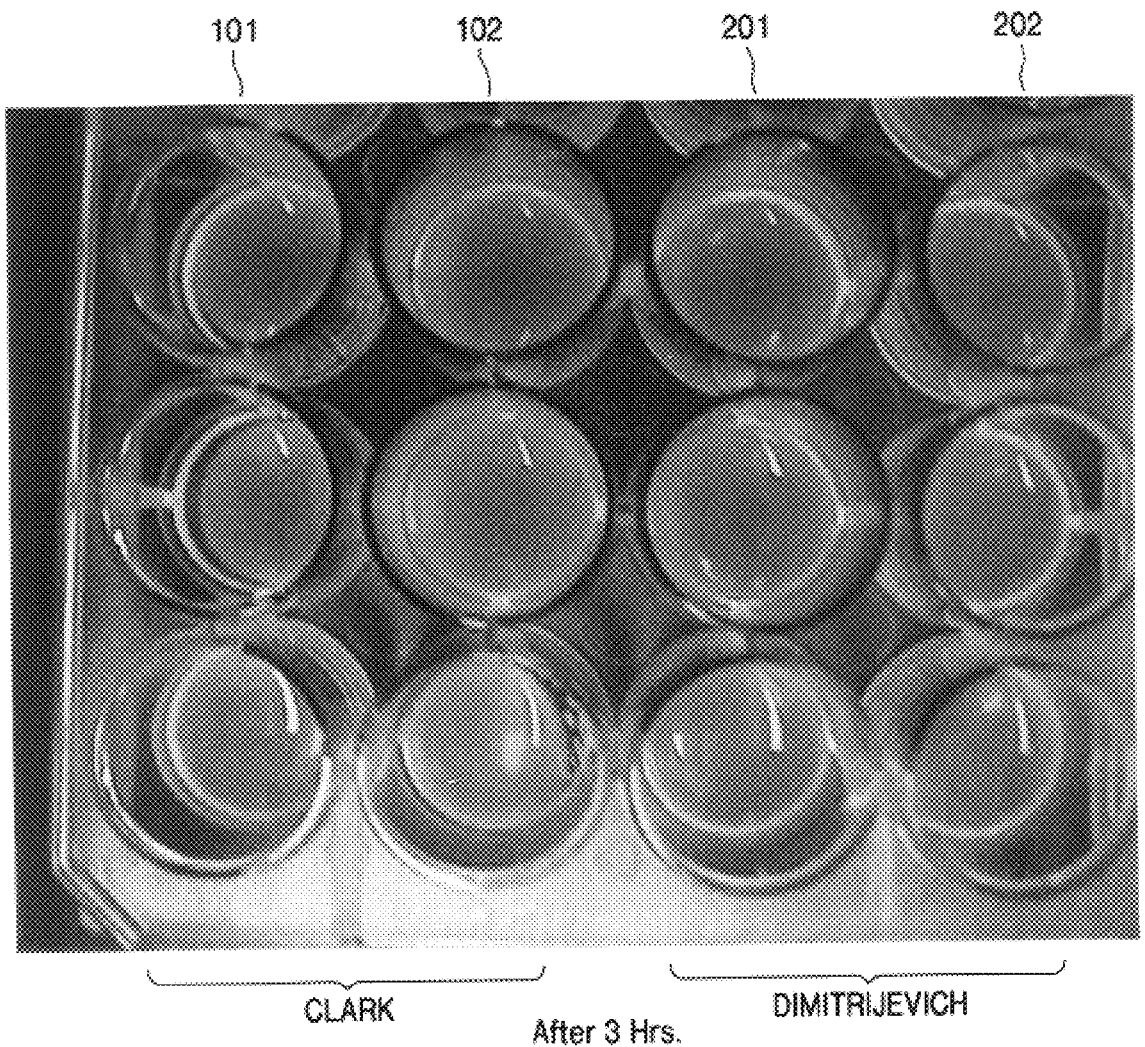
FIG. 20 is a photograph showing surface areas of prior art and present gels at 3 hours.

No significant changes were observed over a period of 30 hours in the surface areas of the gels of the D&G wells (see FIGS. 17 to 19). (Time measurements were taken from the start point of when the wells are judged to have gelled; the starting point for time measurements for the Clark wells proved difficult for the reasons discussed above.) In contrast, significant and variable decreases in surface area of "gels" in the Clark wells were observed as early as 3 hours after set up; the Clark wells in Rows 101 and 102 of FIG. 20 showed substantial non-uniform contraction; in contrast, the six D&G wells shown in Rows 201 and 202 did not exhibit substantive contraction of the gels (similar results were noted for the remaining D&G wells not shown in FIG. 20).

Figure 21:
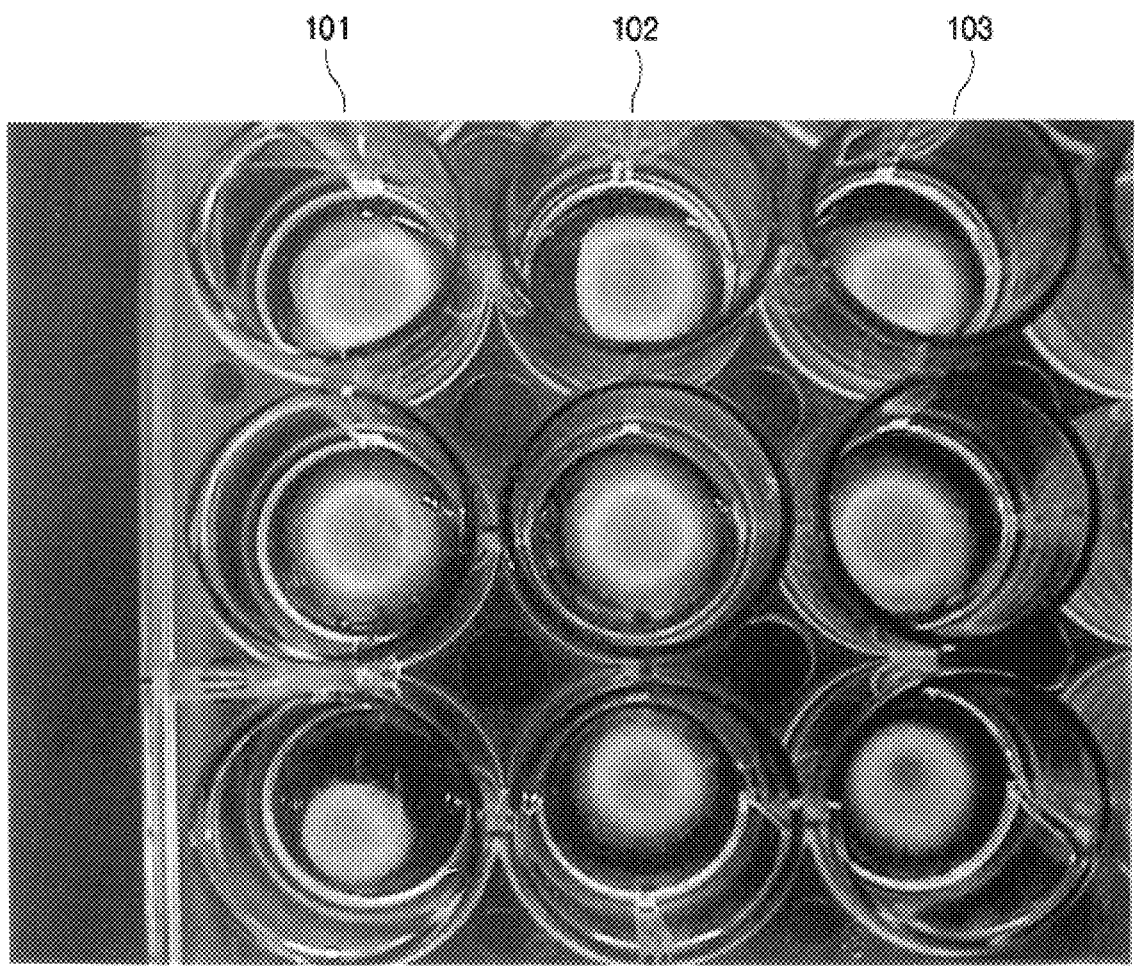
FIG. 21 is a photograph showing surface areas of prior art gels at 7 hours.
Figure 22:
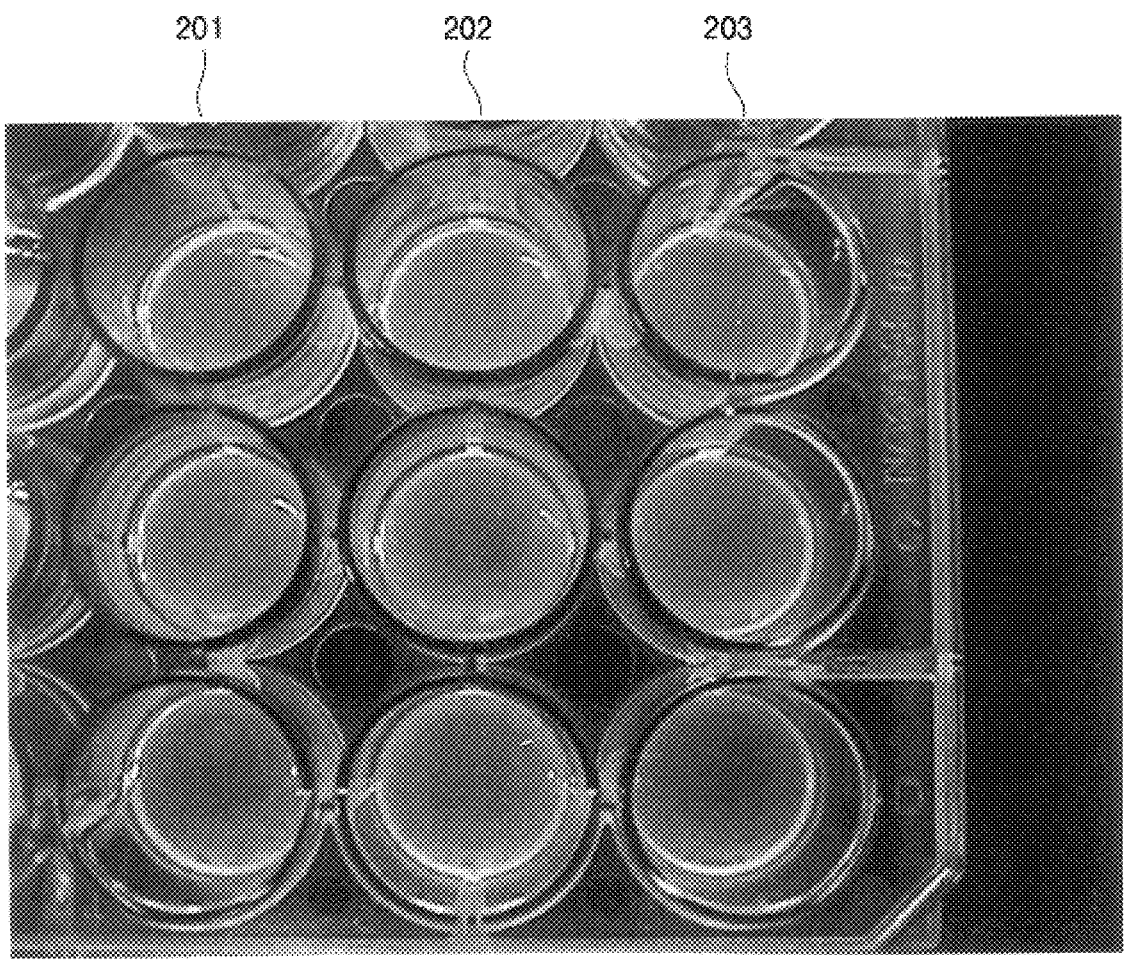
FIG. 22 is a photograph showing surface areas of present gels at 7 hours.

After 7 hours nine of the Clark wells (rows 101, 102, and 103 in FIG. 21) exhibited noticeable non-uniform contraction of the gels. In contrast, after 7 hours (see rows 201, 202; and 203 in FIG. 22) nine of the D&G matrices clearly show non-contraction of the gels (likewise for the tenth D&G well, not shown in FIG. 22).

Figure 23:
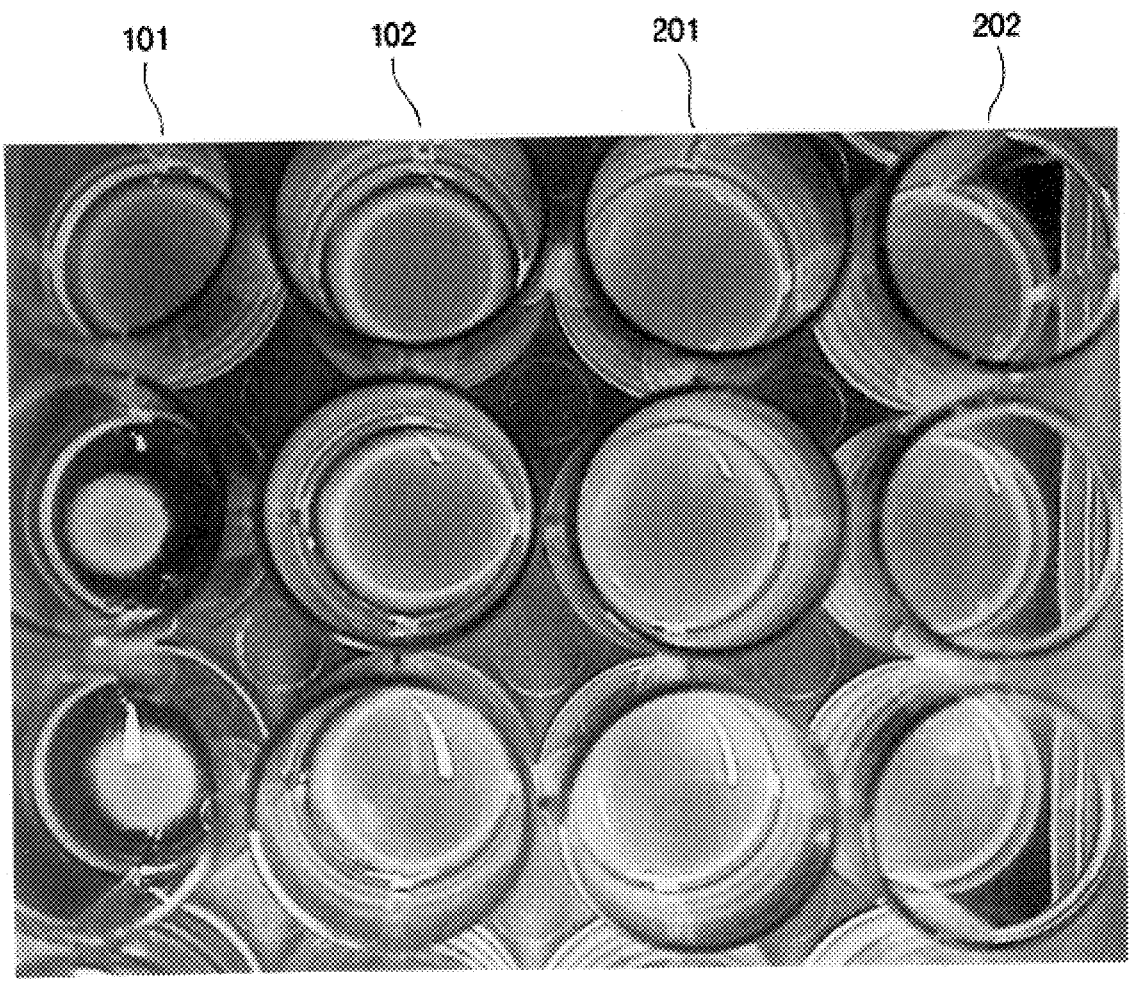
FIG. 23 is a photograph showing surface areas of prior art and present gels at 48 hours.

After 48 hours the Clark matrices exhibit strong non-uniform contraction of the gels (see rows 101 and 102 in FIG. 23). In contrast, after 48 hours the D&G matrices maintain uniform non-contraction of the gels (see rows 201 and 202 in FIG. 23). Thus, the D&G matrices of Example 20 are substantially non-contracting, and exhibit the characteristic of a substantial uniform non-contracting tissue equivalent.

The foregoing is intended to be illustrative of the present invention, but not limiting. Numerous variations and modifications of the present invention may be effected without departing from the true spirit and scope of the invention.

TABLE 6

| Time (Hrs) | Avg % of T = 0 Area Clark Run 1 | Avg % of T = 0 Area Clark Run 2 | Avg % of T = 0 Area Clark Run 1 + 2 |
| --- | --- | --- | --- |
| 0.0 | 100.0 | 100.00 | 100.00 |
| 3.0 | 98.0 | 92.25 | 95.14 |
| 5.0 | 91.3 | 85.65 | 88.46 |
| 7.0 | 90.6 | 82.39 | 86.48 |
| 24.0 | 88.0 | 75.89 | 81.94 |
| 30.0 | 82.1 | 75.51 | 78.79 |

TABLE 8

| Time (Hrs) | Avg % of T = 0 Area Clark Run 1 + 2 | % Ste DEV Clark Runs 1 + 2 |
| --- | --- | --- |
| 0.0 | 100.00 | 0.00 |
| 3.0 | 95.14 | 1.65 |
| 5.0 | 88.46 | 3.61 |
| 7.0 | 86.48 | 3.41 |
| 24.0 | 81.94 | 1.81 |
| 30.0 | 78.79 | 3.21 |

TABLE 9

| Avg % of T = 0 Area Dimitrijevich Run 1 + 2 | % Ste DEV Dimitrijevich Runs 1 + 2 |
| --- | --- |
| 100 | 0.00 |
| 100 | 0.00 |
| 100 | 0.00 |
| 100 | 0.00 |
| 100 | 0.00 |
| 100 | 0.00 |

TABLE 10

Data for summary Graph (FIG. 19)

| Time (Hrs) | Avg Area | Avg Area Clark #2 | Avg Area Dimitrijevich #1 | Avg Area Dimitrijevich #2 |
| --- | --- | --- | --- | --- |
| 0.0 | 201.1 | 201.1 | 201.1 | 201.1 |
| 3.0 | 197.1 | 185.5 | 201.1 | 201.1 |
| 5.0 | 183.7 | 172.2 | 201.1 | 201.1 |
| 7.0 | 182.1 | 165.7 | 201.1 | 201.1 |
| 24.0 | 164.0 | 152.6 | 201.1 | 201.1 |
| 30.0 | 148.7 | 151.8 | 201.1 | 201.1 |

| Time (Hrs) | Ste DEV Clark #1 | Ste DEV Dimitrijevich #1 | Ste DEV Clark #2 | Ste DEV Dimitrijevich #2 |
| --- | --- | --- | --- | --- |
| 0.0 | 0.0 | 0.0 | 0.0 | 0.0 |
| 3.0 | 0.0 | 0.0 | 6.8 | 0.0 |
| 5.0 | 3.3 | 0.0 | 11.0 | 0.0 |
| 7.0 | 4.4 | 0.0 | 9.0 | 0.0 |
| 24.0 | 7.6 | 0.0 | 5.5 | 0.0 |
| 30.0 | 4.3 | 0.0 | 5.5 | 0.0 |

TABLE 7

| Avg % of T = 0 Area Dimitrijevich Run 1 | Avg % of T = 0 Area Dimitrijevich Run 2 | Avg % of T = 0 Area Dimitrijevich Run 1 + 2 | Ste DEV Clark Run 1 | Ste DEV Clark Run 2 | Average Ste Dev Clark | Ste DEV Dimitrijevich Run 1 | Ste DEV Dimitrijevich Run 2 | Average Std Dev Dimitrijevich |
| --- | --- | --- | --- | --- | --- | --- | --- | --- |
| 100.0 | 100.00 | 100.00 | 0.0 | 0.00 | 0.00 | 0.0 | 0.0 | 0.00 |
| 100.0 | 100.00 | 100.00 | 0.0 | 3.30 | 1.65 | 0.0 | 0.0 | 0.00 |
| 100.0 | 100.00 | 100.00 | 1.7 | 5.47 | 3.61 | 0.0 | 0.0 | 0.00 |
| 100.0 | 100.00 | 100.00 | 2.3 | 4.47 | 3.41 | 0.0 | 0.0 | 0.00 |
| 100.0 | 100.00 | 100.00 | 0.9 | 2.76 | 1.81 | 0.0 | 0.0 | 0.00 |
| 100.0 | 100.00 | 100.00 | 3.7 | 2.72 | 3.21 | 0.0 | 0.0 | 0.00 |

TABLE 11

Contraction of Dermal Equivalents
Run #1

Data from Clark DE's Contraction in mm

Repition

| 1 | 2 | 3 | 4 | 5 | 6 | 7 | 8 | 9 |
|---|---|---|---|---|---|---|---|---|
| 0 | 0 | 0 | 0 | 0 | 0 | 0 | 0 | 0 |
| 2 | 2 | 2 | 2 | 2 | 2 | 2 | 2 | 2 |
| 6 | 6 | 6 | 10 | 6 | 6 | 10 | 6 | 6 |
| 8 | 6 | 6 | 10 | 6 | 6 | 11 | 6 | 10 |
| 19 | 13 | 13 | 19 | 13 | 13 | 19 | 13 | 19 |
| 22 | 21 | 21 | 27 | 21 | 22 | 22 | 22 | 24 |

Diameter - Contraction in mm

Repition

| 1 | 2 | 3 | 4 | 5 | 6 | 7 | 8 | 9 |
|---|---|---|---|---|---|---|---|---|
| 160 | 160 | 160 | 160 | 160 | 160 | 160 | 160 | 160 |
| 158 | 158 | 158 | 158 | 158 | 158 | 158 | 158 | 158 |
| 154 | 154 | 154 | 150 | 154 | 154 | 150 | 154 | 154 |
| 152 | 154 | 154 | 150 | 154 | 154 | 149 | 154 | 150 |
| 141 | 147 | 147 | 141 | 147 | 147 | 141 | 147 | 141 |
| 138 | 139 | 139 | 133 | 139 | 138 | 138 | 138 | 136 |

Area Calculated

| Time (Hrs) | Avg Area Clark | Ste DEV Clark | 1 | 2 | 3 | 4 | 5 | 6 | 7 | 8 | 9 |
|---|---|---|---|---|---|---|---|---|---|---|---|
| 0.0 | 201.1 | 0.0 | 201 | 201 | 201 | 201 | 201 | 201 | 201 | 201 | 201 |
| 3.0 | 197.1 | 0.0 | 197 | 197 | 197 | 197 | 197 | 197 | 197 | 197 | 197 |
| 5.0 | 183.7 | 3.3 | 185 | 185 | 185 | 178 | 185 | 185 | 178 | 185 | 185 |
| 7.0 | 182.1 | 4.4 | 182 | 185 | 185 | 178 | 185 | 185 | 174 | 185 | 178 |
| 24.0 | 164.0 | 7.6 | 156 | 170 | 170 | 156 | 170 | 170 | 158 | 170 | 156 |
| 30.0 | 148.7 | 4.3 | 149 | 153 | 153 | 139 | 153 | 149 | 149 | 149 | 146 |

TABLE 12

Figure 24:
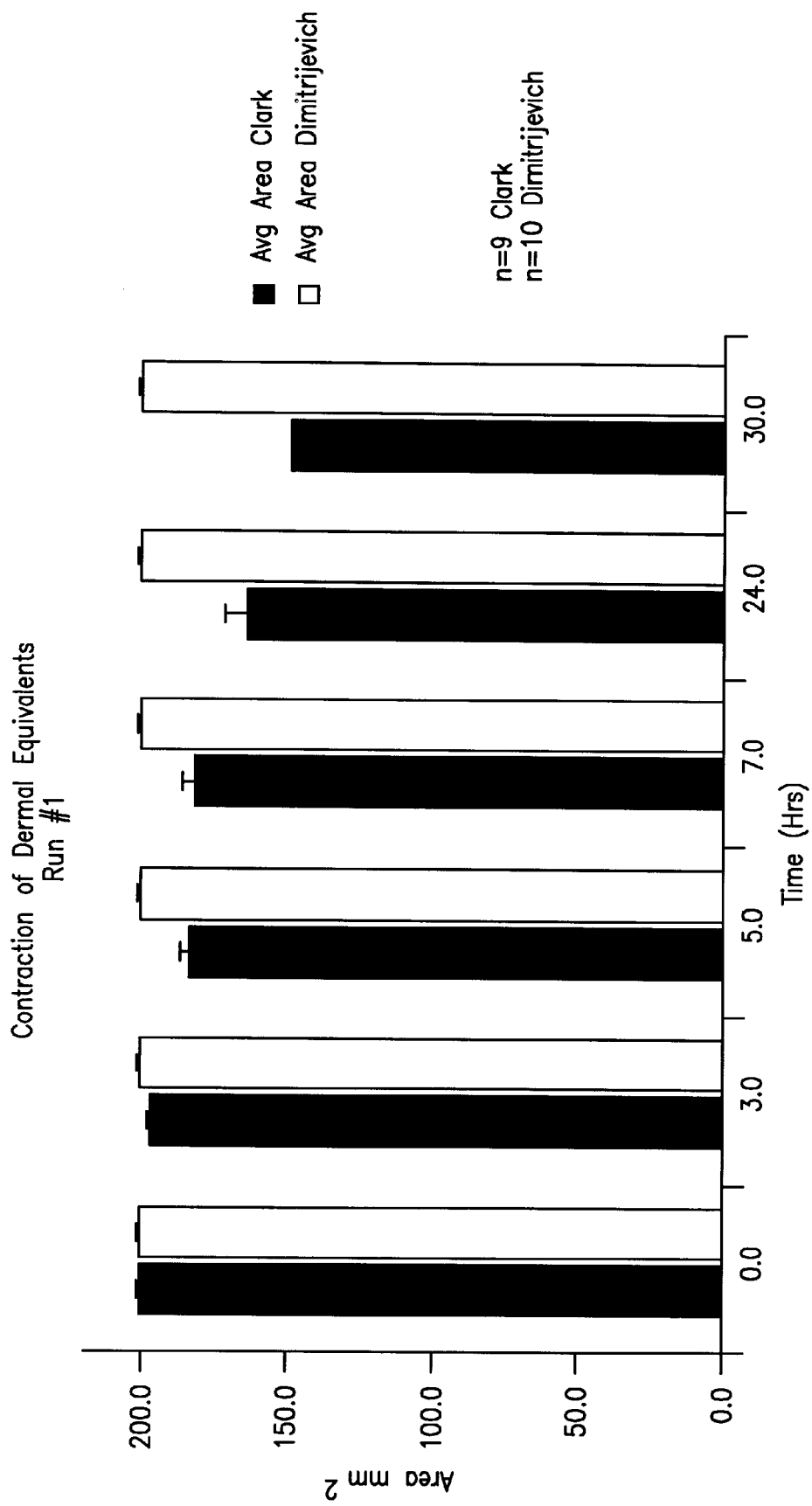
FIG. 24 is a histogram showing contraction of dermal equivalents as per Run #1 (Example 20) over a 30 hour period.

Data Table for Graph 1 (as shown in FIG. 24)

| Time (Hrs) | Avg Area Clark | Avg Area Dimitrijevich | Ste DEV Clark | Ste DEV Dimitrijevich |
|---|---|---|---|---|
| 0.0 | 201.1 | 201.1 | 0.0 | 0.0 |
| 3.0 | 197.1 | 201.1 | 0.0 | 0.0 |
| 5.0 | 183.7 | 201.1 | 3.3 | 0.0 |
| 7.0 | 182.1 | 201.1 | 4.4 | 0.0 |
| 24.0 | 164.0 | 201.1 | 7.6 | 0.0 |
| 30.0 | 148.7 | 201.1 | 4.3 | 0.0 |

| Time (Hrs) | Avg % of T = 0 Area Clark | Ste DEV Clark | % of T = 0 Area | | | |
|---|---|---|---|---|---|---|
| 0 | 100.0 | 0.0 | 100.0 | 100.0 | 100.0 | 100.0 |
| 3 | 98.0 | 0.0 | 98.0 | 98.0 | 98.0 | 98.0 |
| 5 | 91.4 | 1.7 | 92.2 | 92.2 | 92.2 | 88.4 |
| 7 | 90.5 | 2.2 | 90.3 | 92.2 | 92.2 | 88.4 |
| 24 | 81.6 | 3.8 | 77.6 | 84.8 | 84.8 | 77.6 |
| 30 | 74.0 | 2.1 | 74.1 | 75.9 | 75.9 | 69.1 |

| Time (Hrs) | % of T = 0 Area | | | | |
|---|---|---|---|---|---|
| 0 | 100.0 | 100.0 | 100.0 | 100.0 | 100.0 |
| 3 | 98.0 | 98.0 | 98.0 | 98.0 | 98.0 |
| 5 | 92.2 | 92.2 | 88.4 | 92.2 | 92.2 |
| 7 | 92.2 | 92.2 | 86.6 | 92.2 | 88.4 |
| 24 | 84.8 | 84.8 | 77.6 | 84.8 | 77.6 |
| 30 | 75.9 | 74.1 | 74.1 | 74.1 | 72.5 |

TABLE 13

Data Table for Graph 3 (as shown in Fig. 17)

| Time (Hrs) | Avg % of T = 0 Area Clark | Avg % of T = 0 Area Dimitrijevich | Ste DEV Clark | Ste DEV Dimitrijevich |
|---|---|---|---|---|
| 0.0 | 100.0 | 100.0 | 0.0 | 0.0 |
| 3.0 | 98.0 | 100.0 | 0.0 | 0.0 |
| 5.0 | 91.3 | 100.0 | 1.7 | 0.0 |
| 7.0 | 90.6 | 100.0 | 2.3 | 0.0 |
| 24.0 | 88.0 | 100.0 | 0.9 | 0.0 |
| 30.0 | 82.1 | 100.0 | 3.7 | 0.0 |

TABLE 14

Run #1

Data from Dimitrijevich DE's Contraction in mm

| | | | | | Repition | | | | | |
|---|---|---|---|---|---|---|---|---|---|---|
| | 1 | 2 | 3 | 4 | 5 | 6 | 7 | 8 | 9 | 10 |
| | 0.00 | 0.00 | 0.00 | 0.00 | 0.00 | 0.00 | 0.00 | 0.00 | 0.00 | 0.00 |
| | 0.00 | 0.00 | 0.00 | 0.00 | 0.00 | 0.00 | 0.00 | 0.00 | 0.00 | 0.00 |
| | 0.00 | 0.00 | 0.00 | 0.00 | 0.00 | 0.00 | 0.00 | 0.00 | 0.00 | 0.00 |
| | 0.00 | 0.00 | 0.00 | 0.00 | 0.00 | 0.00 | 0.00 | 0.00 | 0.00 | 0.00 |
| | 0.00 | 0.00 | 0.00 | 0.00 | 0.00 | 0.00 | 0.00 | 0.00 | 0.00 | 0.00 |
| | 0.00 | 0.00 | 0.00 | 0.00 | 0.00 | 0.00 | 0.00 | 0.00 | 0.00 | 0.00 |

Diameter - Contraction in mm

| | | | | | Repition | | | | | |
|---|---|---|---|---|---|---|---|---|---|---|
| | 1 | 2 | 3 | 4 | 5 | 6 | 7 | 8 | 9 | 10 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |

| Time (Hrs) | Avg Area Dimitrijevich | Ste DEV Dimitrijevich | \multicolumn{10}{c}{Repition} |
|---|---|---|---|---|---|---|---|---|---|---|---|---|
| | | | 1 | 2 | 3 | 4 | 5 | 6 | 7 | 8 | 9 | 10 |
| 0.0 | 201.1 | 0.0 | 201 | 201 | 201 | 201 | 201 | 201 | 201 | 201 | 201 | 201 |
| 3.0 | 201.1 | 0.0 | 201 | 201 | 201 | 201 | 201 | 201 | 201 | 201 | 201 | 201 |
| 5.0 | 201.1 | 0.0 | 201 | 201 | 201 | 201 | 201 | 201 | 201 | 201 | 201 | 201 |
| 7.0 | 201.1 | 0.0 | 201 | 201 | 201 | 201 | 201 | 201 | 201 | 201 | 201 | 201 |
| 24.0 | 201.1 | 0.0 | 201 | 201 | 201 | 201 | 201 | 201 | 201 | 201 | 201 | 201 |
| 30.0 | 201.1 | 0.0 | 201 | 201 | 201 | 201 | 201 | 201 | 201 | 201 | 201 | 201 |

TABLE 15

| Time (Hrs) | Avg % of T = 0 Area Dimitrijevich | Ste DEV Dimitrijvich | \multicolumn{10}{c}{% of T = 0 Area} |
|---|---|---|---|---|---|---|---|---|---|---|---|---|
| 0.0 | 100.0 | 0.0 | 100.0 | 100.0 | 100.0 | 100.0 | 100.0 | 100.0 | 100.0 | 100.0 | 100.0 | 100.0 |
| 3.0 | 100.0 | 0.0 | 100.0 | 100.0 | 100.0 | 100.0 | 100.0 | 100.0 | 100.0 | 100.0 | 100.0 | 100.0 |
| 5.0 | 100.0 | 0.0 | 100.0 | 100.0 | 100.0 | 100.0 | 100.0 | 100.0 | 100.0 | 100.0 | 100.0 | 100.0 |
| 7.0 | 100.0 | 0.0 | 100.0 | 100.0 | 100.0 | 100.0 | 100.0 | 100.0 | 100.0 | 100.0 | 100.0 | 100.0 |
| 24.0 | 100.0 | 0.0 | 100.0 | 100.0 | 100.0 | 100.0 | 100.0 | 100.0 | 100.0 | 100.0 | 100.0 | 100.0 |
| 30.0 | 100.0 | 0.0 | 100.0 | 100.0 | 100.0 | 100.0 | 100.0 | 100.0 | 100.0 | 100.0 | 100.0 | 100.0 |

TABLE 16

Contraction of Dermal Equivalents
Run #2

Data from Clark EQ's Contraction in mm

| Time (Hrs) | \multicolumn{9}{c}{Repitition} |
|---|---|---|---|---|---|---|---|---|---|
| | 1 | 2 | 3 | 4 | 5 | 6 | 7 | 8 | 9 |
| 0 | 0 | 0 | 0 | 0 | 0 | 0 | 0 | 0 | 0 |
| 3.0 | 6 | 3 | 3 | 6 | 10 | 10 | 6 | 10 | 3 |
| 5.0 | 10 | 10 | 16 | 10 | 13 | 16 | 13 | 19 | 3 |
| 7.0 | 13 | 16 | 16 | 16 | 19 | 16 | 13 | 19 | 6 |

TABLE 16-continued

Contraction of Dermal Equivalents
Run #2

| | | | | | | | | | |
|---|---|---|---|---|---|---|---|---|---|
| 24.0 | | 16 | 17 | 22 | 19 | 22 | 22 | 22 | 22 | 22 |
| 30.0 | | 16 | 19 | 22 | 19 | 22 | 22 | 24 | 22 | 22 |

Diameter - Contraction in mm

| | | Repitition | | | | | | | |
|---|---|---|---|---|---|---|---|---|---|
| | 1 | 2 | 3 | 4 | 5 | 6 | 7 | 8 | 9 |
| | 160.0 | 160.0 | 160.0 | 160.0 | 160.0 | 160.0 | 150.0 | 160.0 | 160.0 |
| | 153.7 | 156.8 | 156.8 | 153.7 | 150.5 | 150.5 | 153.7 | 150.5 | 156.8 |
| | 150.5 | 150.5 | 144.1 | 150.5 | 147.3 | 144.1 | 147.3 | 141.0 | 156.8 |
| | 147.3 | 144.1 | 144.1 | 144.1 | 141.0 | 144.1 | 147.3 | 141.0 | 153.7 |
| | 144.1 | 142.5 | 137.8 | 141.0 | 137.8 | 137.8 | 137.8 | 137.8 | 137.8 |
| | 144.1 | 141.0 | 137.8 | 141.0 | 137.8 | 137.8 | 136.2 | 137.8 | 137.8 |

Area Calculated

| Time (Hrs) | Avg Area Clark | Ste DEV Clark | Repitition | | | | | | | | |
|---|---|---|---|---|---|---|---|---|---|---|---|
| | | | 1 | 2 | 3 | 4 | 5 | 6 | 7 | 8 | 9 |
| 0 | 201.1 | 0.0 | 201.1 | 201 | 201 | 201 | 201 | 201 | 201 | 201 | 201 |
| 3.0 | 185.5 | 6.6 | 185.4 | 193 | 193 | 185 | 178 | 178 | 185 | 178 | 193 |
| 5.0 | 172.2 | 11.0 | 177.8 | 178 | 163 | 178 | 170 | 163 | 170 | 156 | 193 |
| 7.0 | 165.7 | 9.0 | 170.4 | 163 | 163 | 163 | 156 | 163 | 170 | 156 | 165 |
| 24.0 | 152.6 | 5.5 | 163.1 | 160 | 149 | 156 | 149 | 149 | 149 | 149 | 149 |
| 30.0 | 151.8 | 5.5 | 163.1 | 156 | 149 | 156 | 149 | 149 | 146 | 149 | 149 |

TABLE 17

Figure 25:
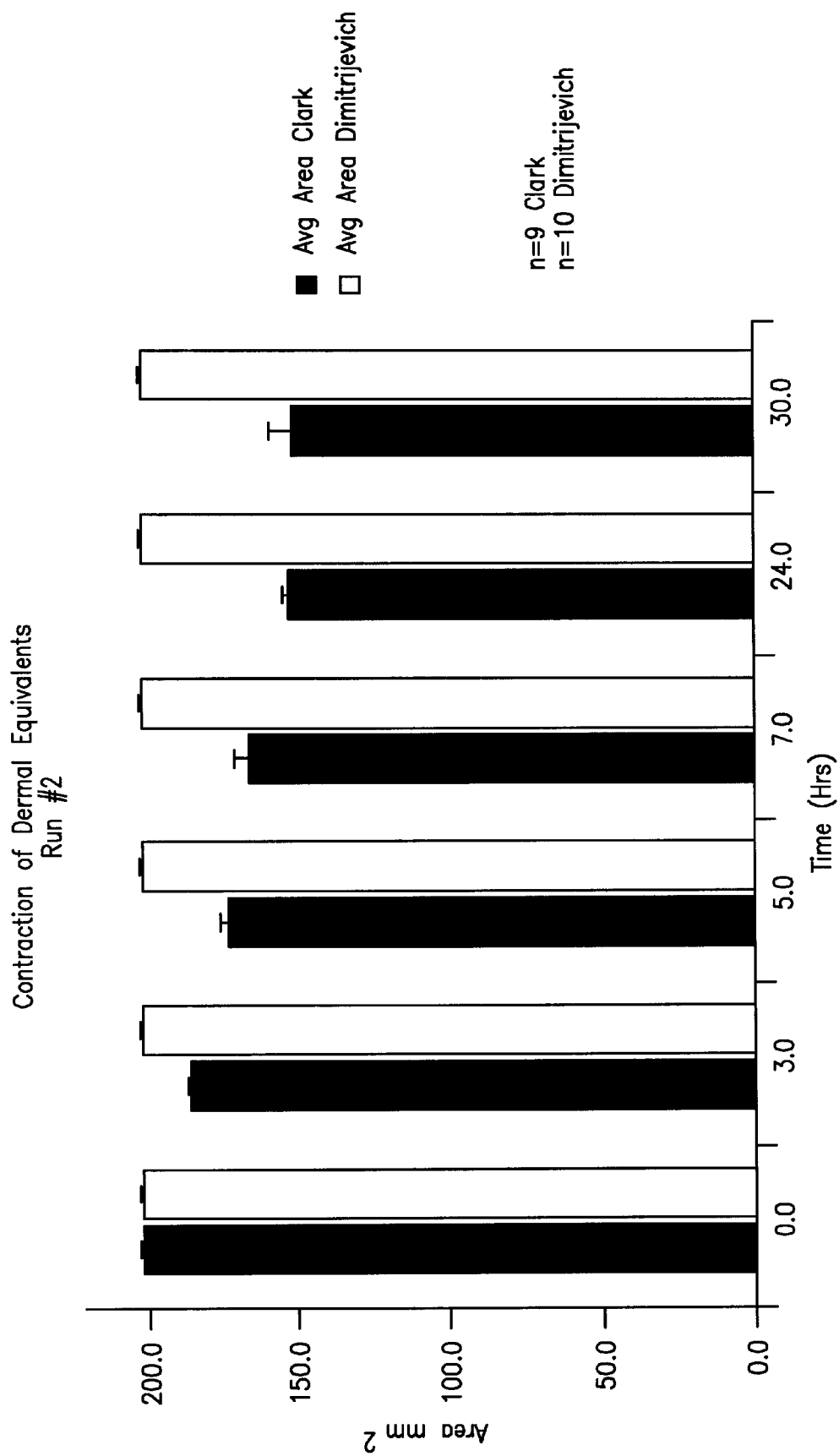

Contraction of Dermal Equivalents
Run #2
Data Table for Graph 2 (as shown in FIG. 25)

| Time (Hrs) | Avg Area Clark | Avg Area Dimitrijevich | Ste DEV Clark | Ste DEV Dimitrijevich |
|---|---|---|---|---|
| 0.0 | 201.1 | 201.1 | 0.0 | 0.0 |
| 3.0 | 185.5 | 201.1 | 6.6 | 0.0 |
| 5.0 | 172.2 | 201.1 | 11.0 | 0.0 |
| 7.0 | 165.7 | 201.1 | 9.0 | 0.0 |
| 24.0 | 152.6 | 201.1 | 5.5 | 0.0 |
| 30.0 | 151.8 | 201.1 | 5.5 | 0.0 |

| Time (Hrs) | Avg % of T = 0 Area Clark | Ste DEV Clark | % of T = 0 Area | | | |
|---|---|---|---|---|---|---|
| 0.0 | 100.0 | 0.0 | 100.0 | 100.0 | 100.0 | 100.0 |
| 3.0 | 92.2 | 3.3 | 92.2 | 96.1 | 96.1 | 92.2 |
| 5.0 | 85.6 | 5.5 | 88.4 | 88.4 | 81.1 | 88.4 |
| 7.0 | 82.4 | 4.5 | 84.8 | 81.1 | 81.1 | 81.1 |
| 24.0 | 75.9 | 2.8 | 81.1 | 79.4 | 74.1 | 77.6 |
| 30.0 | 75.5 | 2.7 | 81.1 | 77.6 | 74.1 | 77.6 |

| Time (Hrs) | % of T = 0 Area | | | | |
|---|---|---|---|---|---|
| 0.0 | 100.0 | 100.0 | 100.0 | 100.0 | 100.0 |
| 3.0 | 88.4 | 88.4 | 92.2 | 88.4 | 96.1 |
| 5.0 | 84.8 | 81.1 | 84.8 | 77.6 | 96.1 |

TABLE 17-continued

Contraction of Dermal Equivalents
Run #2
Data Table for Graph 2 (as shown in FIG. 25)

| 7.0 | 77.6 | 81.1 | 84.8 | 77.6 | 92.2 |
|---|---|---|---|---|---|
| 24.0 | 74.1 | 74.1 | 74.1 | 74.1 | 74.1 |
| 30.0 | 74.1 | 74.1 | 72.5 | 74.1 | 74.1 |

TABLE 18

Data Table for Graph 4 (as shown in Fig. 18)

| Time (Hrs) | Avg % of T = 0 Area Clark | Avg % of T = 0 Area Dimitrijevich | Ste DEV Clark | Ste DEV Dimitrijevich |
|---|---|---|---|---|
| 0.0 | 100.0 | 100.0 | 0.0 | 0.0 |
| 3.0 | 92.2 | 100.0 | 3.3 | 0.0 |
| 5.0 | 85.6 | 100.0 | 5.5 | 0.0 |
| 7.0 | 82.4 | 100.0 | 4.5 | 0.0 |
| 24.0 | 75.9 | 100.0 | 2.8 | 0.0 |
| 30.0 | 75.5 | 100.0 | 2.7 | 0.0 |

TABLE 19

Run #2

| | | | | | Contraction in mm | | | | | |
|---|---|---|---|---|---|---|---|---|---|---|
| | | | | | Repetition | | | | | |
| | 1 | 2 | 3 | 4 | 5 | 6 | 7 | 8 | 9 | 10 |
| | 0 | 0 | 0 | 0 | 0 | 0 | 0 | 0 | 0 | 0 |
| | 0 | 0 | 0 | 0 | 0 | 0 | 0 | 0 | 0 | 0 |
| | 0 | 0 | 0 | 0 | 0 | 0 | 0 | 0 | 0 | 0 |
| | 0 | 0 | 0 | 0 | 0 | 0 | 0 | 0 | 0 | 0 |
| | 0 | 0 | 0 | 0 | 0 | 0 | 0 | 0 | 0 | 0 |
| | 0 | 0 | 0 | 0 | 0 | 0 | 0 | 0 | 0 | 0 |

| | | | | Diameter - Contraction in mm | | | | | | |
|---|---|---|---|---|---|---|---|---|---|---|
| | | | | Repetition | | | | | | |
| | 1 | 2 | 3 | 4 | 5 | 6 | 7 | 8 | 9 | 10 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |
| | 160.0 | 160.0 | 160.0 | 160.0 | 160.0 | 160.0 | 160.0 | 160.0 | 160.0 | 160.0 |

| | | | | | ea Calculated | | | | | | |
|---|---|---|---|---|---|---|---|---|---|---|---|
| Time | Avg Area | Ste DEV | | | | Repitition | | | | | |
| (Hrs) | Dimitrijevich | Dimitrijevich | 1 | 2 | 3 | 4 | 5 | 6 | 7 | 8 | 9 | 10 |
| 0.0 | 201.1 | 0.0 | 201 | 201 | 201 | 201 | 201 | 201 | 201 | 201 | 201 | 201 |
| 3.0 | 201.1 | 0.0 | 201 | 201 | 201 | 201 | 201 | 201 | 201 | 201 | 201 | 201 |
| 5.0 | 201.1 | 0.0 | 201 | 201 | 201 | 201 | 201 | 201 | 201 | 201 | 201 | 201 |
| 7.0 | 201.1 | 0.0 | 201 | 201 | 201 | 201 | 201 | 201 | 201 | 201 | 201 | 201 |
| 24.0 | 201.1 | 0.0 | 201 | 201 | 201 | 201 | 201 | 201 | 201 | 201 | 201 | 201 |
| 30.0 | 201.1 | 0.0 | 201 | 201 | 201 | 201 | 201 | 201 | 201 | 201 | 201 | 201 |

TABLE 20

| Time (Hrs) | Avg % of T = 0 Dimitrijevich | Ste DEV Dimitrijevich | | | | | | | | | | |
|---|---|---|---|---|---|---|---|---|---|---|---|---|
| 0.00 | 100.0 | 0.0 | 100.0 | 100.0 | 100.0 | 100.0 | 100.0 | 100.0 | 100.0 | 100.0 | 100.0 |
| 3.00 | 100.0 | 0.0 | 100.0 | 100.0 | 100.0 | 100.0 | 100.0 | 100.0 | 100.0 | 100.0 | 100.0 |
| 5.00 | 100.0 | 0.0 | 100.0 | 100.0 | 100.0 | 100.0 | 100.0 | 100.0 | 100.0 | 100.0 | 100.0 |
| 7.00 | 100.0 | 0.0 | 100.0 | 100.0 | 100.0 | 100.0 | 100.0 | 100.0 | 100.0 | 100.0 | 100.0 |
| 24.00 | 100.0 | 0.0 | 100.0 | 100.0 | 100.0 | 100.0 | 100.0 | 100.0 | 100.0 | 100.0 | 100.0 |
| 30.00 | 100.0 | 0.0 | 100.0 | 100.0 | 100.0 | 100.0 | 100.0 | 100.0 | 100.0 | 100.0 | 100.0 |

We claim:

1. A method of making a tissue equivalent which comprises the steps of combining an aqueous suspension of initial mesenchymal cells in a substantially serum-free nutrient medium at a temperature below about ambient temperature with a solution of collagenous material to produce a gelable admixture;
solidifying the admixture by gelation to a translucent collagenous matrix;
thereafter combining said translucent collagenous matrix with an aqueous suspension of other mesenchymal cells;
and incubating the resulting combination for a time period sufficient for said other mesenchymal cells to attach to said collagenous matrix, wherein the cell density of the tissue equivalent is in the range of about $1.0 \times 10^5$ cells/ml and the collagen concentration of the tissue equivalent is in the range of about 3 to about 5 mg/ml.

2. The method of claim 1 wherein the collagenous material is a member of the group consisting of collagen I, collagen III, collagen IV, fibrin, fibronectin and mixtures thereof.

3. The method of claim 1 wherein an additional collagenous material is combined with said translucent collagenous matrix.

4. The method of claim 3 wherein the additional collagenous material is a member of the group consisting of collagen I, collagen III, collagen IV, fibrin, fibronectin and mixtures thereof.

5. The method of claim 1 wherein the additional collagenous material is collagen IV.

6. The method of claim 1 wherein the initial mesenchymal cells are members of the group consisting of fibroblasts, keratinocytes, keratocytes, melanocytes, corneal fibroblasts, corneal epithelial cells and corneal endothelial cells.

7. The method of claim 1 wherein the other mesenchymal cells are members of the group consisting of fibroblasts, keratinocytes, melanocytes, corneal fibroblasts, corneal epithelial cells and corneal endothelial cells.

8. The method of claim 1 wherein the other mesenchymal cells are keratinocytes.

9. The method of claim 1 comprising the additional step of contacting the produced tissue equivalent with further mesenchymal cells which are members of the group consisting of fibroblasts, keratinocytes, melanocytes, corneal fibroblasts, corneal epithelial cells and corneal endothelial cells.

10. The method of claim 9 wherein the initial mesenchymal cells are corneal fibroblasts.

11. The method of claim 9 wherein the other mesenchymal cells are corneal endothelial cells.

12. The method of claim 9 wherein the further mesenchymal cells are melanocytes.

13. The method of claim 10 wherein the other mesenchymal cells are corneal epithelial cells.

14. The method of claim 3 wherein the additional collagenous material is a mixture of fibronectin and laminin.

15. The method of claim 3 wherein the additional collagenous material is a mixture of fibronectin, collagen and laminin.

16. A substantially non-contracting tissue equivalent which comprises an uncontracted collagenous matrix and a plurality of mesenchymal cells retrained within said matrix; said collagenous matrix being substantially free from covalent crosslinks and dissociated by mild treatment with collagenase, wherein the substantially non-contractile characteristic of said tissue equivalent is independent of cell density in the range of about $1.0 \times 10^5$ to about $5.0 \times 10^5$ cells/ml, and is independent of collagen concentration in the range of about 3 to about 5 mg/ml.

17. The tissue equivalent of claim 16, wherein the mesenchymal cells are members of the group consisting of fibroblasts, keratinocytes, melanocytes and mixtures thereof.

18. The tissue equivalent of claim 16, wherein the matrix is a member of the group consisting of collagen I, collagen III, collagen IV, fibrin, fibronectin and mixtures thereof.

19. The tissue equivalent of claim 16, wherein the mesenchymal cells are fibroblasts and the matrix is collagen I.

20. The tissue equivalent of claim 16, wherein a second cellular component comprising keratinocytes is present.

21. The tissue equivalent of claim 16, wherein the collagenous matrix is constitute by collagen I and collagen IV.

22. The tissue equivalent of claim 21, wherein the mesenchymal cells are members of the group consisting of fibroblasts, keratinocytes, melanocytes, corneal fibroblasts, corneal epithelial cells, corneal endothelial cells, and mixtures thereof.

23. The substantially non-contracting tissue equivalent of claim 21 wherein the mesenchymal cells are corneal fibroblasts and corneal endothelial cells.

24. The tissue equivalent of claim 21, which has been formed serum-free media and viably maintained in media comprising Ham's F-12 media supplemented with about 6.0 g/L glucose, no more than 2 mM calcium, about 50 μgml α-ketoglutarate, about 27 mg/ml glycine, 50 μg/ml ascorbate and no more than about 5% serum.

25. The tissue equivalent of claim 21, wherein said collagenous matrix is a three-dimensional collagenous matrix.

26. A method of making a tissue equivalent which comprises the steps of combining an aqueous suspension of mesenchymal cells in a substantially serum-free nutrient medium at a temperature below about ambient temperature with a solution of collagenous material to produce a gelable admixture; and solidifying the admixture by gelation at a pH of about 7 and a temperature of about 37° C. to a translucent matrix;

wherein the cell density of the tissue equivalent is in the range of about $1.0 \times 10^5$ cells/ml and the collagen concentration of the tissue equivalent is in the range of about 3 to about 5 mg/ml.

27. The method in accordance with claim 26 wherein the nutrient medium contains no more than about 2 mM of calcium.

28. The method of claim 26 wherein the mesenchymal cells are members of the group consisting of fibroblasts, keratinocytes, melanocytes and mixtures thereof.

29. The method of claim 26, wherein the collagenous material is a member of the group consisting of collagen I, collagen III, collagen IV, fibrin, fibronectin and mixtures thereof.

30. The method of claim 26, wherein the mesenchymal cells are fibroblasts and the collagenous material is collagen I.

31. The method of claim 26 wherein the solidification is effected in an incubator at about 37° C.

32. The method in accordance with claim 26 wherein the culture medium exhibits an oxygen partial pressure of at least about 300 millimeters of mercury but no more than about 1250 millimeters of mercury.

33. The tissue equivalent of claim 16 wherein a second cellular component comprising keratinocytes is present.

34. The substantially non-contracting tissue equivalent of claim 16 wherein the collagenous matrix is constituted by collagen I and collagen IV.

35. The substantially non-contracting tissue equivalent of claim 34 wherein the mesenchymal cells are members of the group consisting of fibroblasts, keratinocytes, melanocytes, corneal fibroblasts, corneal epithelial cells, corneal endothelial cells, and mixtures thereof.

36. The substantially non-contracting tissue equivalent of claim 34 wherein the mesenchymal cells are corneal fibroblasts and corneal endothelial cells.

* * * * *

UNITED STATES PATENT AND TRADEMARK OFFICE
CERTIFICATE OF CORRECTION

PATENT NO. : 6,471,958 B2
DATED : October 29, 2002
INVENTOR(S) : S. Dan Dimitrijevich et al.

It is certified that error appears in the above-identified patent and that said Letters Patent is hereby corrected as shown below:

<u>Title page,</u>
Item [*] Notice, should read as follows: -- Subject to any disclaimer, the term of this patent is extended or adjusted under 35 U.S.C. 154(b) by 66 days. --

<u>Column 10,</u>
Line 7, "Imi," should be -- III, --.

<u>Column 19,</u>
Line 43, "25 cm" should be -- 25 $cm^2$ --.

<u>Column 23,</u>
Line 54, "10 (lays." should be -- 10 days. --.

<u>Column 24,</u>
Line 21, "16 square mmm)." should be -- 16 square mm). --
Line 27, "5 mnls" should be -- 5 mls --.

<u>Columns 27-28,</u>
Table 11, under Area Calculated, Repition 7, "158" should be -- 156 --.

<u>Columns 31-32,</u>
Table 16-continued, under Area Calculated, Repitition 9, "165" should be -- 185 --.

<u>Column 36,</u>
Line 2, after "formed" insert -- in --.
Line 4, "50 $\mu$gml" should be -- 50 $\mu$g/ml --.

Signed and Sealed this

First Day of June, 2004

JON W. DUDAS
*Acting Director of the United States Patent and Trademark Office*